United States Patent
Johnson et al.

(10) Patent No.: US 6,541,021 B1
(45) Date of Patent: Apr. 1, 2003

(54) DEVICES AND METHODS FOR PAIN MANAGEMENT

(75) Inventors: Randolph Mellus Johnson, Half Moon Bay, CA (US); Felix Theeuwes, Los Altos Hills, CA (US)

(73) Assignee: Durect Corporation, Cupertino, CA (US)

( * ) Notice: Subject to any disclaimer, the term of this patent is extended or adjusted under 35 U.S.C. 154(b) by 0 days.

(21) Appl. No.: 09/522,535

(22) Filed: Mar. 10, 2000

Related U.S. Application Data

(60) Provisional application No. 60/125,589, filed on Mar. 18, 1999.

(51) Int. Cl.⁷ .............................. A61F 13/00; A61F 2/00; A61K 9/22; A61K 9/24; A61N 43/42
(52) U.S. Cl. ........................ 424/422; 424/423; 424/424; 424/425; 424/449; 424/473; 424/484; 424/450; 604/890.1; 604/891.1; 604/892.1; 514/282
(58) Field of Search ..................... 424/449, 443, 424/423; 514/12

(56) References Cited

U.S. PATENT DOCUMENTS

| | | |
|---|---|---|
| 3,141,823 A | 7/1964 | Janssen et al. |
| 3,760,984 A | 9/1973 | Theeuwes |
| 3,845,770 A | 11/1974 | Theeuwes et al. |
| 3,916,899 A | 11/1975 | Theeuwes et al. |
| 3,923,426 A | 12/1975 | Theeuwes |
| 3,987,790 A | 10/1976 | Eckenhoff et al. |
| 3,995,631 A | 12/1976 | Higuchi et al. |
| 3,998,834 A | 12/1976 | Janssen et al. |
| 4,016,880 A | 4/1977 | Theeuwes et al. |
| 4,036,228 A | 7/1977 | Theeuwes |
| 4,111,202 A | 9/1978 | Theeuwes |
| 4,111,203 A | 9/1978 | Theeuwes |
| 4,167,574 A | 9/1979 | Janssens |

(List continued on next page.)

FOREIGN PATENT DOCUMENTS

| | | |
|---|---|---|
| EP | WO 97/49391 | * 12/1997 |
| EP | WO 98/51246 | * 11/1998 |
| WO | WO 97/27840 | 8/1997 |
| WO | WO 97/49391 | 12/1997 |
| WO | WO 98/51246 | 11/1998 |
| WO | WO 99/36071 | 7/1999 |

OTHER PUBLICATIONS

Paix et al., 1995, "Subcutaneous fentanyl and subfentanyl infusion substitution for morph . . . ", vol. 3: 263–269.*

(List continued on next page.)

*Primary Examiner*—Thurman K. Page
*Assistant Examiner*—Isis Ghapi
(74) *Attorney, Agent, or Firm*—Bozicevic, Field & Francis LLP; Carol L. Francis

(57) ABSTRACT

The invention features devices and methods for the systemic delivery of fentanyl or a fentanyl congener (e.g., sufentanil) to treat pain. In the present invention, a drug formulation comprising fentanyl or a fentanyl congener is stored within a drug delivery device (e.g., contained in a reservoir or impregnated within a matrix within the controlled drug delivery device). The drug formulation comprises an amount of drug sufficient for treatment and is stable at body temperatures (i.e., no unacceptable degradation) for the entire pre-selected treatment period. The drug delivery devices store the drug formulation safely (e.g., without dose dumping), provide sufficient protection from bodily processes to prevent unacceptable degradation of the formulation, and release the drug formulation in a controlled fashion at a therapeutically effective rate to treat pain. In use, the drug delivery device is implanted in the subject's body at an implantation site, and the drug formulation is released from the drug delivery device to a delivery site. The delivery site may be the same as, near, or distant from the implantation site. Once released at the delivery site, the drug formulation enters the systemic circulation and is transported to the site of action in the body to modulate the pain response (e.g., the brain or other pain sensory location).

88 Claims, 6 Drawing Sheets

U.S. PATENT DOCUMENTS

| | | | |
|---|---|---|---|
| 4,203,440 A | 5/1980 | Theeuwes |
| 4,203,442 A | 5/1980 | Michaels |
| 4,210,139 A | 7/1980 | Higuchi |
| 4,327,725 A | 5/1982 | Cortese et al. |
| 4,360,019 A | 11/1982 | Portner et al. |
| 4,487,603 A | 12/1984 | Harris |
| 4,576,951 A | 3/1986 | Rovati et al. |
| 4,582,835 A | 4/1986 | Lewis et al. |
| 4,588,580 A | 5/1986 | Gale et al. |
| 4,627,850 A | 12/1986 | Deters et al. |
| 4,681,560 A | 7/1987 | Schulte et al. |
| 4,692,147 A | 9/1987 | Duggan |
| 4,725,852 A | 2/1988 | Gamblin et al. |
| 4,769,372 A | 9/1988 | Kreek |
| 4,781,924 A | 11/1988 | Lee |
| 4,865,845 A | 9/1989 | Eckenhoff et al. |
| 5,057,318 A | 10/1991 | Magruder et al. |
| 5,059,423 A | 10/1991 | Magruder et al. |
| 5,112,614 A | 5/1992 | Magruder et al. |
| 5,137,727 A | 8/1992 | Eckenhoff |
| 5,180,716 A | 1/1993 | Yaksh et al. |
| 5,187,177 A | 2/1993 | Garzaran |
| 5,234,692 A | 8/1993 | Magruder et al. |
| 5,234,693 A | 8/1993 | Magruder et al. |
| 5,346,903 A | 9/1994 | Ackerman et al. |
| 5,356,635 A | * 10/1994 | Raman et al. |
| 5,451,408 A | 9/1995 | Mezei et al. |
| 5,472,943 A | 12/1995 | Crain et al. |
| 5,486,362 A | 1/1996 | Kitchell et al. |
| 5,487,739 A | 1/1996 | Aebischer et al. |
| 5,512,578 A | 4/1996 | Crain et al. |
| 5,580,876 A | 12/1996 | Crain et al. |
| 5,589,480 A | 12/1996 | Elkhoury et al. |
| 5,633,000 A | 5/1997 | Grossman et al. |
| 5,660,854 A | 8/1997 | Haynes et al. |
| 5,672,167 A | 9/1997 | Athayde et al. |
| 5,728,396 A | 3/1998 | Peery et al. |
| 5,729,396 A | 3/1998 | Dudley et al. |
| 5,747,058 A | 5/1998 | Tipton et al. |
| 5,767,125 A | 6/1998 | Crain et al. |
| 5,798,114 A | 8/1998 | Elsheny et al. |
| 5,858,388 A | 1/1999 | Grossman et al. |
| 5,866,164 A | 2/1999 | Kuczynski et al. |
| 5,980,927 A | 11/1999 | Nelson et al. |
| 5,985,305 A | 11/1999 | Peery et al. |
| RE36,547 E | 2/2000 | Crain et al. |
| 6,096,756 A | 8/2000 | Crain et al. |
| 6,203,813 B1 | * 3/2001 | Gooberman |
| 6,245,351 B1 | * 6/2001 | Nara et al. |
| 6,436,091 B1 | 8/2002 | Harper et al. |

OTHER PUBLICATIONS

Anderson et al. (1998). "Alternate Routes of Opioid Administration in Palliative Care: Pharmacologic and Clinical Concerns" *J. Pharmaceutical Care in Pain Symptom Control*, vol. 6(1):5–21.

Bansinath, et al. (1989). "Hyperglycemia does not modify the pupillary effects of $\mu$ and $\kappa$ opiate agonists in mice" *J. Ocular Pharmacology*, vol. 5(1): 33–43.

Bruera et al. (1987), "Use of the subcutaneous route of the administration of narcotics in patients with cancer pain" *Cancer*, vol. 62(2): 407–411.

Cherny et al. (1995). "Opioid pharmacotherapy in the management of cancer pain" *Cancer*, vol. 76(7): 1283–1293.

Clotz et al. (1991). "Clinical uses of fentanyl, sufentanil, and alfentanil" *Clinical Pharmacy*, vol. 10: 581–593.

Coda et al. (1997). "Comparative efficacy of patient–controlled administration of morphine, hydromorphone, or sufentanil for the treatment of oral mucositis pain following bone marrow transplantation" *Pain*, vol. 72: 333–346.

Crane (1994). "Intermittent subcutaneous infusion of opioids in hospice home care: An effective, economical, manageable option" *Am. J. Hospice & Palliative Care*, vol. Jan./Feb. 8–12.

Dhasmana et al. (1987). "Gastrointestinal transit following inthrathecal or subcutaneous narcotic analgesics" *Arch. Int. Pharmacodyn.*, vol. 286: 152–161.

Fuginaga et al. (1988). "Reproductive and teratogenic effects of sufentanil and alfentanil in Sprague–Dawley rate" *Anesth Analg.* vol. 67: 166–169.

Geller et al. (1993). "A randomized double–blind comparison of epidural sufentanil versus intravenous sufentanil or epidural fentanyl analgesia after major abdominal surgery" *Anest. Analg*, vol. 76: 1243–1250.

Kerr et al. (1988). "Continuous narcotic infusion with patient–controlled analgesia for chronic cancer pain in out-patients" *Annals of Internal Medicine*, vol. 108;554–557.

Leelanuntakit (1996). "Management of cancer–related pain with transdermal fentnyl" *J. Med. Assoc. Thai*, vol. 79(6): 341–346.

Moulin et al. (1992). "Subcutaneous narcotic infusions for cancer pain: treatment outcome and guidelines for use" *Can. Med. Assoc. J.*, vol. 146(6): 891–897.

Mucha et al. (1990). "Parker and Radow test of drug withdrawal aversion: Opposite effect in rats chronically infused with sufentanil or amphetamine" *Pharmacology Biochem. & Behavior*, vol. 35: 219–224.

Paix et al. (1995). "Subcutaneous fentanyl and sufentanil infusion substitution for morphine intolerance in cancer pain management" *Pain*, vol. 3:263–269.

Satterlee (1991). "Criteria for use of fentanyl citrate, sufentanil citrate, and alfentanil hydrochlorid*a*" *Clinical Pharmacy*, vol. 10:635–637.

Sjøgren et al. (1994). "Disappearance of morphine–induced hyperalgesia after discontinuing or substituting morphine with other opioid agonists" *Pain*, vol. 59:313–316.

Taverne et al. (1992). "Comparative absorption and distribution pharmacokinetics of intravenous and epidural sufentanil for major abdomincal surgery" *Clin. Pharmacokinet.*, vol. 23(3): 231–237.

Van den Hoogen et al. (1987). "Epidural and subcutaneous morphine, meperidine (pethidine), fentany and sufentanil in the rat: Analgesia and other in vivo pharmacologic effects" *Anesthesiology*, vol. 66: 186–194.

Van den Hoogen et al. (1988). "Respiratory effects of epidural and subcutaneous morphine, meperidine (pethidine), fentanyl and sufentanil in the rat" *Anest Analg*, vol. 67: 1071–1078.

Wagner et al. (1997). "Pharmacokinetics and pharmacodynamics of sedatives and analgescics in the treatment of agitated critically ill patients" *Clin. Pharmacokinet*, vol. 33(6):426–453.

Willens et al. (1993). "Pharmacodynamics, pharmacokinetics, and clinical uses of fentanyl, sufentanil, and alfentanil" *Heart & Lung*, vol. 22(3):239–251.

Zeiler et al. (1991). "Kontinuierliche peridurale sufentanil–applikation zur postoperativen analgesie" *Anaesthesist*, vol. 40:543–548.

Ahmedzai (1997), "New approaches to pain control in patients with cancer." *Eur. J. Cancer*, 33(6):S8–S14.

Anderson et al. (1998), "Alternate routes of opioid administration in palliative care: pharmacologic and clinical concerns." *J. Pharmaceut. Care Pain Sympt. Control.* 6:5–21.

Coyle et al. (1994). "Subcutaneous opioid infusions at home." *Oncology*, 8:21–27.

Fine (1997), "Fentanyl in the treatment of cancer pain." *Sem. Oncol.*, 24(16):S16–S27.

Finley (1990), "Pain management with spinally administered opioids." *Am. J. Hosp. Pharm.*, 47(1):S14–S17.

Jeal et al. (1997). "Transdermal fentanyl. A review of its pharmacologic properties and therapeutic efficacy in pain control." *Drugs*, 53:109–138.

Kerr et al. (1988). "Continuous narcotic infusion with patient–controlled analgesia for chronic cancer pain in outpatients." *Ann. Intern. Med.*, 108:554–557.

Kingery (1997), "A critical review of controlled clinical trials for peripheral neuropathic pain and complex regional pain syndromes." *Pain*, 73:123–139.

Martin et al. (1983), "Epidural and intrathecal narcotics." *Can. Anaesth. Soc. J.*, 30:662–673.

Shaw (1993), "Treatment of intractable cancer pain by electronically controlled parenteral infusion of analgesic drugs." *Cancer*, 72:3416–3425.

Skaer (1993), "Management of pain in the cancer patient." *Clin. Ther.*, 15:638–649.

Slattery et al. (1985), "Newer methods of delivery of opiates for relief of pain." *Drugs*, 30:539–551.

Vertafridda et al. (1987), "Intraspinal morphine for cancer pain." *Acta Anaesthesiol Scand.*, 31(85):47–53.

* cited by examiner

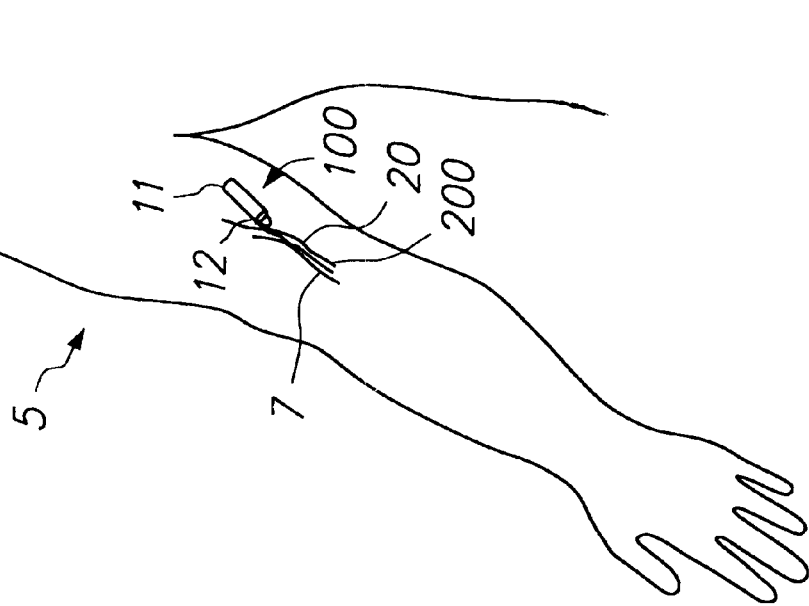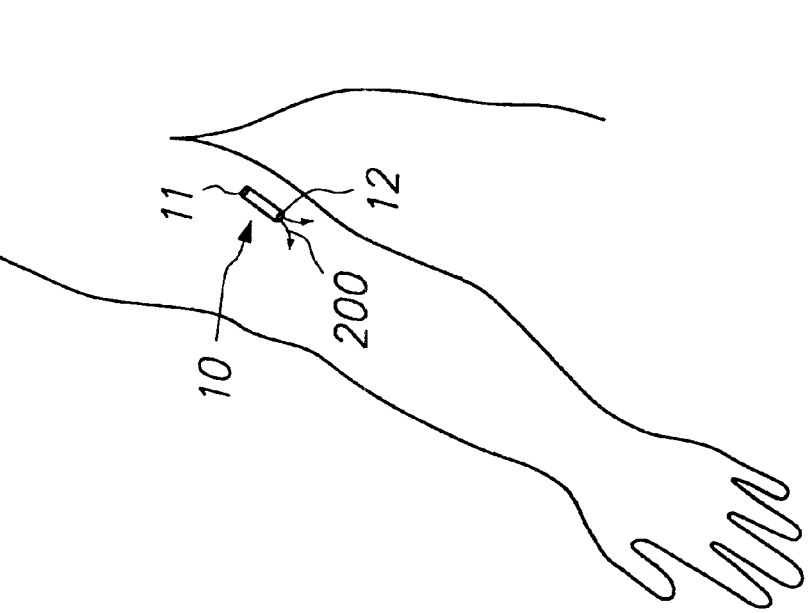

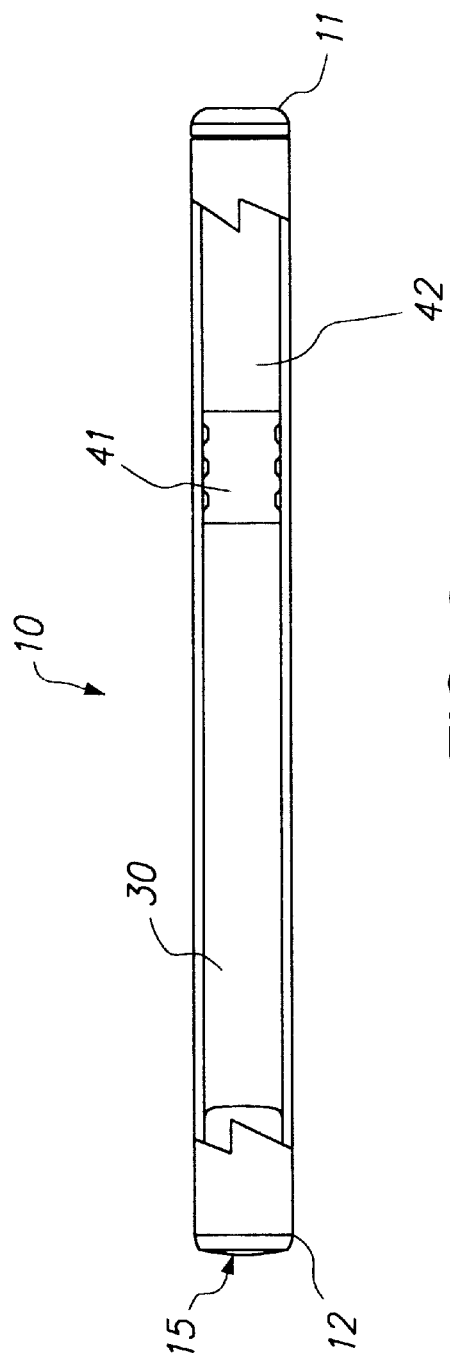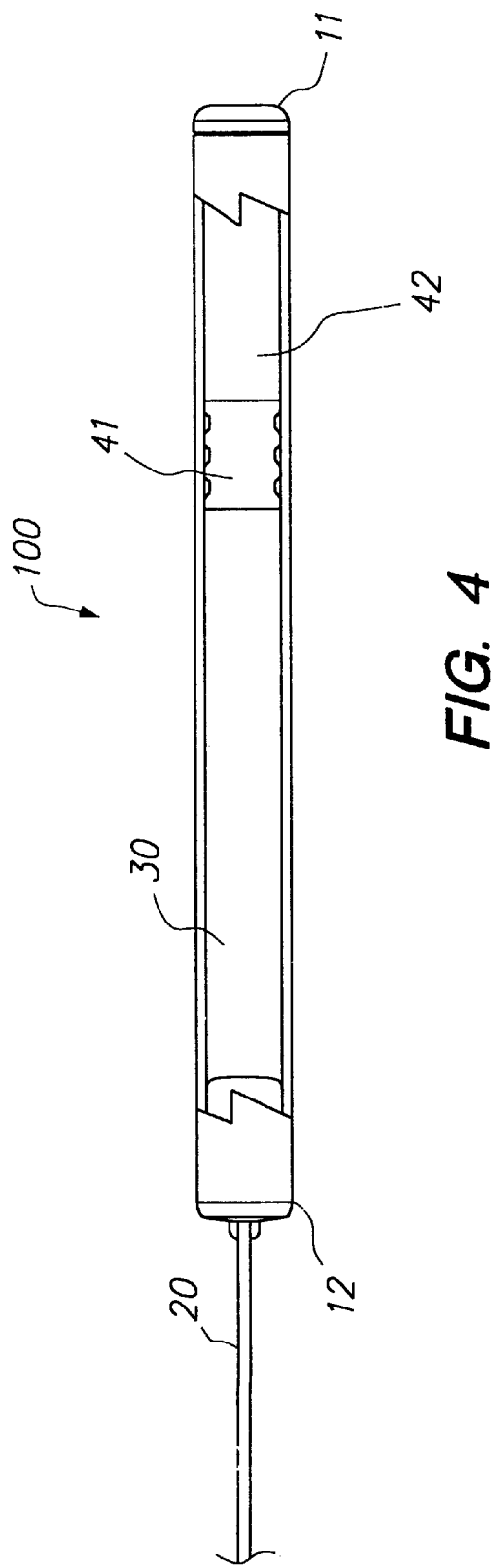

DEVICES AND METHODS FOR PAIN MANAGEMENT

CROSS-REFERENCE TO RELATED APPLICATIONS

This application claims the benefit of U.S. Provisional Application Ser. No. 60/125,589, filed Mar. 18, 1999, which application incorporated herein by reference.

FIELD OF THE INVENTION

The invention relates to devices and methods for the management of pain.

BACKGROUND OF THE INVENTION

Many medications are used for the treatment of pain, ranging from well known, over-the-counter compounds such as aspirin, acetaminophen, ibuprofen and other non-steroidal anti-inflammatory compounds to the newly developed chemical entities such as the cyclooxygenase. II inhibitor compounds. Opiates in various forms, including opium, heroine and morphine which derive from the opium poppy, have very powerful analgesic properties. Opiates have been widely used for anesthesia as well for the treatment of pain, especially where the pain is very severe. In addition to these natural opiates, many synthetic opioids have since been synthesized including methadone, fentanyl and congeners of fentanyl such as sufentanil, alfentanil, lofentanil, carfentanil, remifentanil, etc. Of the opioids, morphine is still the drug of choice for management of pain at least in part due to its low cost, the ability of the drug to provide relief from pain of a variety of origins, and the vast experience with this drug. Despite its therapeutic advantages and vast experience with the drug, many pain management experts believe that morphine and other opioids are under-prescribed for patients who require long-term pain therapy.

One reason for underprescription is the risk of the side effects associated with long-term administration of opioids in general, such as development of opiate tolerance, dependence, constipation, and/or other undesirable side effects (see, e.g., Moulin et al. 1992 Can Med. Assoc. J. 146:891–7). Patients who develop opioid tolerance require increased doses to achieve a satisfactory analgesic effect, and risk the development of further undesirable side effects such as respiratory depression, which can be life threatening. Physical dependence, which is related to factors such as the dose administered and the length of the administration period, can generally only be resolved by discontinuing opioid administration, which in turn results in the onset of severely painful withdrawal symptoms. Other side effects that can be associated with administration of opioids include reduced cough reflex, bronchial spasms, nausea, vomiting, peripheral vasodilation, orthostatic hypotension, vagal impact on the heart, contraction of smooth muscles (sphincters), reduced peristaltic motility in the gastrointestinal tract (e.g., constipation), urinary retention, changes in regulation of body temperature and sleep pattern, and release of histamine, adrenalin, and anti-diuretic hormone. The negative effects on respiratory function especially impact postoperative patients, who are particularly susceptible to depression of respiratory function. Even where the concerns regarding side effects might be outweighed by the serious need for pain relief as in terminally ill patients, many doctors still avoid prescribing opioids due to concerns of abuse of surplus medication by others in contact with the patient, or even that their frequent prescription of the drug might lead to criminal investigation.

In addition to the disadvantages listed above pertaining to opioids in general, morphine itself has also been associated with particular side effects, at times so severe as to make such therapy intolerable, especially for patients who are on long-term pain therapy or who require high doses of medication to obtain relief. Some of these side effects associated with morphine usage, particularly at high doses, include nausea and vomiting (see for example Paix et al. (1995) Pain 63:263–9) and severe constipation. In addition, Sjorgen et al. (1994 Pain 59:313–316) have reported the phenomena of hyperalgesia (increased response to certain stimulus which is not normally painful), allodynia (sensation of pain felt even when stimulus is not normally painful) and myoclonus associated with morphine use. It has been hypothesized that morphine and its metabolites may induce such abnormal sensitivity (see, e.g., Sjorgen et al. (1994) Pain 59:313–316).

Fentanyl and its congeners were originally developed as anesthesia agents, and are generally used in the United States for the limited purposes of intravenous administration in balanced general anesthesia, as a primary anesthetic, or, in the case of sufentanil, for epidural administration during labor and delivery. However, these drugs also have powerful analgesic properties and are several hundred or thousand times more potent than morphine depending on the particular congener. A few studies have in fact suggested that fentanyl and its congeners be used instead of morphine due to their increased potency and decreased side effects relative to morphine (see e.g., Sjorgen et al. (1994) Pain 59:313–316 and Paix et al. (1995) Pain 63:263–9). Fentanyl and its congeners are, however, more difficult to administer than morphine since they are not orally absorbed, are extremely potent (requiring very precise, accurate dosing of small amounts) and have very short half lives in the body thus requiring frequent dosing. For these reasons, conventional methods for delivery of opioid analgesics are inadequate to meet these delivery requirements. For example, fentanyl has been administered in single, small intravenous doses, but this method of administration, besides being impractical for long-term therapy, results in a short duration of action and rapid recovery due to a redistribution into fat stores and a rapid decline in plasma concentration. The development of transdermal patch delivery technology allowed fentanyl to be delivered continuously through the skin (e.g., the commercial Duragesic™ transdermal patch). Since the transdermal delivery method provided for constant drug delivery, it was a marked improvement relative to bolus injection; however, transdermal delivery also has several limitations. For example, transdermal delivery is disadvantageous in that the dose of drug that can be delivered is limited by the available skin surface area, thus making transdermal delivery suitable for low-to-medium opioid dose requirements, but often inadequate for more high dose requirements. In addition, transdermal delivery of drug is disadvantageous in that there is a delay in obtaining steady state plasma concentrations upon initiation of therapy, as well as a prolonged period of continued effect even after removal of the patch. Other problems associated with transdermal delivery include skin irritation, loss of adhesion after exposure to moisture (e.g., perspiration, bathing) the potential for diversion of drug for illicit purposes and patient distaste for the unsightliness of highly visible patches.

While subcutaneous infusion of fentanyl and sufentanil have been the subject of experimentation on a limited basis, the methods disclosed in the prior art are impractical as long-term pain therapies. Paix et al. (1995 Pain 63:263–9), for example, discloses the use of subcutaneous fentanyl and sufentanil as an alternative therapy in a small number of patients who suffered significant side effects associated with administration of morphine. In Paix et al., the drug was infused into the subcutaneous space at relatively large volume rates (e.g., on the order of 3 mL/day to 40 mL/day) via an external syringe driver. The treatment method disclosed by Paix et al. has several major disadvantages that render it impractical for long-term therapy. First, the provision of drug from an external source adversely affects mobility of the patient and is therefore inconvenient for ambulatory patients, increases the risk of infections at the subcutaneous delivery site and provides an opportunity for drug to be diverted for illicit uses. Second, the infusion of large volumes of fluid may result in tissue damage or edema at the site of infusion. In addition, the absorptive capacity of the subcutaneous space limits the volume of fluid that can be delivered (see, e.g., Anderson et al., supra), and this volumetric limitation can in turn limit the amount of drug that can be administered (e.g., in Paix et al., more potent opioids were administered to some patients requiring high doses since the volume of morphine required was too large to be effectively absorbed in the subcutaneous tissues).

As is evident from the above, there is a great need for devices and methods for effective and practical management of pain, particularly pain of long duration, with better efficacy and reduced side effects. The present invention addresses this problem.

SUMMARY OF THE INVENTION

The invention features devices and methods for the systemic delivery of fentanyl or a fentanyl congener (e.g., sufentanil) to treat pain. In the present invention, a drug formulation comprising fentanyl or a fentanyl congener is stored within a drug delivery device (e.g., contained in a reservoir or impregnated within a matrix within the controlled drug delivery device). The drug formulation comprises an amount of drug sufficient for treatment and is stable at body temperatures (i.e., no unacceptable degradation) for the entire pre-selected treatment period. The drug delivery devices store the drug formulation safely (e.g., without dose dumping), provide sufficient protection from bodily processes to prevent unacceptable degradation of the formulation, and release the drug formulation in a controlled fashion at a therapeutically effective rate to treat pain. In use, the drug delivery device is implanted in the subject's body at an implantation site, and the drug formulation is released from the drug delivery device to a delivery site. The delivery site may be the same as, near, or distant from the implantation site. Once released at the delivery site, the drug formulation enters the systemic circulation and is transported to the site of action in the body to modulate the pain response (e.g., the brain or other pain sensory location).

In one aspect the invention features devices for and methods of treating pain in a subject suffering from pain comprising systemic delivery of a formulation comprising fentanyl or fentanyl congener to the subject via an implantable drug delivery device, where such formulation is delivered at a rate sufficient to ameliorate pain. In specific-embodiments, the formulation comprises sufentanil, which can be administered at a rate of from about 0.01 μg per hour to 200 μg per hour.

In another aspect, the invention features devices for and methods of treating pain by systemic delivery of a formulation comprising fentanyl or fentanyl congener to the subject via an implantable drug delivery device for a pre-selected period at a low volume rate (e.g., from about 0.01 μl/day to 2 ml/day).

In another aspect, the invention features devices for and methods of treating pain in a subject comprising the steps of implanting a drug delivery device at an implantation site in the body of a subject, where the drug delivery device is capable of controlled drug release; and delivering a formulation comprising fentanyl or a fentanyl congener from the device to a delivery site for entering into the systematic circulation in an amount effective to alleviate pain in the subject.

In various exemplary embodiments of the invention and various aspects thereof, drug of the drug formulation administered is delivered at a low dose rate due the potency of the subject drugs, e.g., from about 0.01 μg/hr or 0.1 μg/hr, 0.25 μg/hr, 1 μg/hr, generally up to about 200 μg/hr. Specific ranges of amount of drug delivered will vary depending upon, for example, the potency and other properties of the drug used and the therapeutic requirements of the subject. In one specific embodiment, the formulation comprises sufentanil and, in a specific embodiment, is delivered at a rate of from about 0.01 μg/hr or 0.1 μg/hr, 0.25 μg/hr, 1 μg/hr, generally up to about 200 μg/hr.

In another exemplary embodiment, the drug formulation is delivered at a low volume rate e.g., a volume rate of from about 0.01 μl/day to about 2 ml/day.

In another exemplary embodiment, delivery of the formulation is substantially continuous, and can be for a pre-selected administration period ranging from several hours to years, preferably from about 4 weeks to 12 months.

The drug delivery device can be any implantable device, which device can be based on, for example, diffusive, erodible or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

Pain amenable to alleviation includes, but is not necessarily limited to various types of acute or chronic pain, including cancer pain, inflammatory disease pain, neuropathic pain, nociceptive pain, postoperative pain, iatrogenic pain, complex regional pain syndrome, failed-back pain, soft tissue pain, joint pain, bone pain, central pain, injury pain, arthritic pain, hereditary disease, infectious disease, headache, causalgia, hyperesthesia, sympathetic dystrophy, phantom limb syndrome, and denervation. This invention is particularly useful in the treatment of pain of long duration or chronic pain.

A primary object of the invention is provide a method for convenient, long-term management of pain.

One advantage of the invention is that the devices and methods described herein provide effective management of pain by administration of a relatively small quantity of fentanyl or a fentanyl congener (e.g., sufentanil), providing adequate pain relief and an improvement in adverse side effects relative to morphine. Given the adverse effects of opioid analgesics, this advantage is of considerable benefit to those requiring pain relief, particularly in relatively long term (e.g., 1–4 months) pain situations. Furthermore, the method may be more cost-effective, and thus may make pain management available to a broader population.

Another advantage of the invention is that the invention can be used to deliver relatively small quantities of fentanyl and fentanyl congeners accurately and precisely and thus safely delivering such drugs despite the extreme potency of these drugs compared to morphine. Thus, the invention allows for the convenient use of these drugs for treatment of pain ranging in severity from mild to severe.

One particularly surprising advantage of the invention is that an amount of fentanyl or a fentanyl congener sufficient to provide a relatively long duration of therapy can be stored safely and stably within the body and without deleterious effect given the high potency of the subject compounds.

Another notable advantage of the invention is that the use of an implantable drug delivery device avoids the need for placement of external needles and/or catheters in the subject, which might provide sites susceptible to infection. In addition, use of an implanted device increases patient compliance with a prescribed therapeutic regimen, substantially decreases or completely avoids the risk of abuse of the drug by the patient or others in contact with the patient, and affords greater mobility and easier outpatient management.

Another advantage of the invention is that fentanyl or a fentanyl congener can be delivered into the systemic circulation with such accuracy and precision and at such low quantities as to permit long-term use of such compounds to treat pain.

A further advantage is that a therapeutically effective dose of fentanyl and fentanyl congeners can be delivered at such relatively low volume rates, e.g., from about 0.01 µl/day to 2 ml/day so as to minimize tissue disturbance or trauma.

Another advantage is that fentanyl and fentanyl congeners (e.g., sufentanil) delivery according to the invention provides for effective drug delivery to provide the desired therapeutic effect while avoiding local irritation.

Another advantage of the invention is that substantially continuous delivery of small quantities of fentanyl or fentanyl congener (e.g., sufentanil) is effective in long-term (e.g., chronic) administration (e.g., from several weeks or from about 1 to 12 months or more).

Another advantage of the invention is that the marked potency of the selected opioids (fentanyl, sufentanil, or other fentanyl congener) relative to other opioids such as morphine allows for its administration at effective doses in small amounts and volumes that make it a convenient therapy.

The method of the invention is also advantageous in that since the selected drugs (e.g., sufentanil) are highly lipophilic relative to other opioids, thus facilitating delivery of the drug across the blood-brain barrier. For example, the octanol/water partition coefficient of sufentanil is 1,727, compared to a coefficient of 1.4 for morphine. Systemic administration (e.g., by subcutaneous delivery) of certain lipophilic fentanyl congeners, e.g., sufentanil, may be as effective as if the drug were delivered directly to the central nervous system.

Yet another advantage is that the invention provides for precise delivery of the selected fentanyl-comprising or fentanyl congener-comprising formulation, thus allowing delivery of lower doses and/or for delivery of precisely metered doses at consistent delivery volume rates (e.g., on the order of microliters to milliliters per hour).

Still another advantage is that the invention may decrease the severity or incidence of side effects normally associated with use of morphine in pain management.

These and other objects, advantages and features of the present invention will become apparent to those persons skilled in the art upon reading the details of the methodology and compositions as more fully set forth below.

BRIEF DESCRIPTION OF THE DRAWINGS

FIG. 1 illustrates systemic delivery of drug using an implanted drug delivery device.

FIG. 2 is a perspective view of an exemplary drug delivery device useful in the present invention.

FIG. 3 illustrates intravenous delivery using a drug delivery device implanted subcutaneously via a catheter positioned for delivery of drug intravenously.

FIG. 4 is a cut-away view of an exemplary drug delivery device comprising a catheter.

DESCRIPTION OF THE PREFERRED EMBODIMENTS

Figure 5:
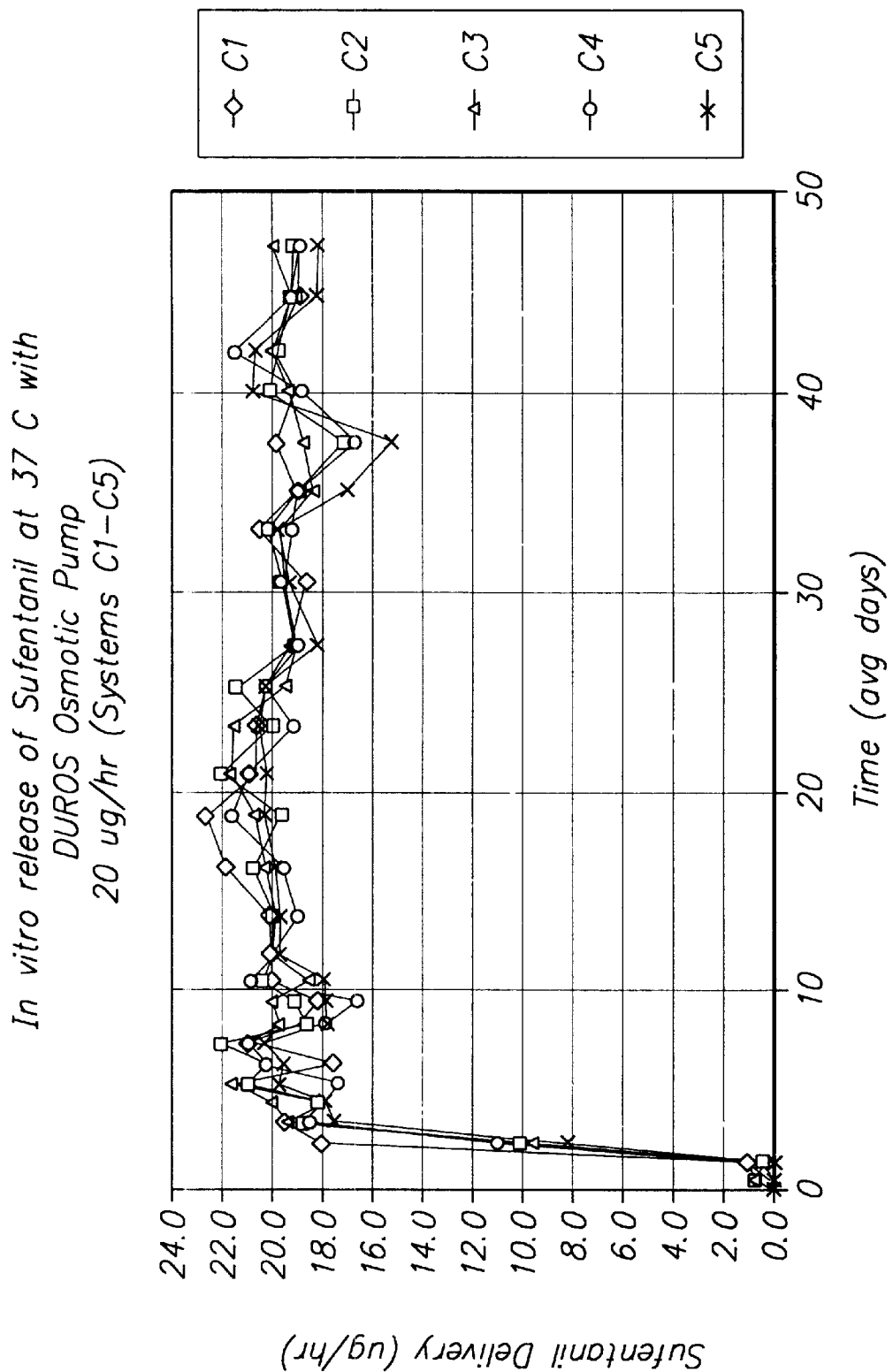
FIG. 5 is a graph showing release of sufentanil from an exemplary osmotic pump at a rate of 20 µg/hr.

Before the present device and methods for treatment of pain are described, it is to be understood that this invention is not limited to the specific methodology, devices, therapeutic formulations, and pain syndromes described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a drug delivery device" includes a plurality of such devices and reference to "the method of delivery" includes reference to equivalent steps and methods known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the compositions and methodologies which are described in the publications which might be used in connection with the presently described invention. The publications discussed herein are provided solely for their disclosure prior to the filing date of the present application. Nothing herein is to be construed as an admission that the invention is not entitled to antedate such a disclosure by virtue of prior invention.

Definitions

The term "drug" as used herein is generally meant to refer to fentanyl or a fentanyl congener (e.g., sufentanil, alfentanil, lofentanil, carfentanil, remifentanil, trefentanil, and mirfentanil), as well as formulations comprising one or more of these compounds. Use of "drug" or the phrase "fentanyl or fentanyl congener" is not meant to be limiting to use of, or formulations comprising, only one of these selected opioid compounds. Furthermore, reference to fentanyl alone or to a selected fentanyl congener alone, e.g., reference to "sufentanil," is understood to be only exemplary of the drugs suitable for delivery according to the methods of the invention, and is not meant to be limiting in any way.

The term "subject" is meant any subject, generally a mammal (e.g., human, canine, feline, equine, bovine, etc.), in which management of pain is desired.

The term "systemic delivery" is meant to encompass all parenteral routes of delivery which permit drug to enter into the systemic circulation, e.g., intravenous, intra-arterial, intramuscular, subcutaneous, intra-adipose tissue, intra-lymphatic, etc.

The term "therapeutically effective amount" is meant an amount of a therapeutic agent, or a rate of delivery of a therapeutic agent, effective to facilitate a desired therapeutic effect. The precise desired therapeutic effect (e.g., the degree of pain relief, and source of the pain relieved, etc.) will vary according to the condition to be treated, the formulation to be administered, and a variety of other factors that are appreciated by those of ordinary skill in the art. In general, the method of the invention involves the suppression or mitigation of pain in a subject suffering from pain that may be associated with any of a variety of identifiable or unidentifiable etiologies.

The term "pain management or treatment" is used here to generally describe regression, suppression, or mitigation of pain so as to make the subject more comfortable as determined by subjective criteria, objective criteria, or both. In general, pain is assessed subjectively by patient report, with the health professional taking into consideration the patient's age, cultural background, environment, and other psychological background factors known to alter a person's subjective reaction to pain.

"Delivery site" as used herein is meant to refer to an area of the body to which drug is delivered for entry into the systemic circulation, e.g., a site which allows systemic access of drug delivered to the site. Exemplary delivery sites compatible with systemic delivery of drug include, but are not necessarily limited to, subcutaneous, intravenous, intra-arterial, intra-muscular, intra-adipose tissue, and intra-lymphatic sites.

The term "implantation site" is used to refer to a site within the body of a subject at which a drug delivery device is introduced and positioned.

"Drug delivery device" as used herein is meant to any implantable device suitable for delivering the formulations for pain management according to the invention. "Drug delivery device" thus encompasses any implantable device with any mechanism of action including diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

"Patterned" or "temporal" as used in the context of drug delivery is meant delivery of drug in a pattern, generally a substantially regular pattern, over a pre-selected period of time (e.g., other than a period associated with, for example a bolus injection). "Patterned" or "temporal" drug delivery is meant to encompass delivery of drug at an increasing, decreasing, substantially constant, or pulsatile, rate or range of rates (e.g., amount of drug per unit time, or volume of drug formulation for a unit time), and further encompasses delivery that is continuous or substantially continuous, or chronic.

The term "controlled drug delivery device" is meant to encompass any device wherein the release (e.g., rate, timing of release) of a drug or other desired substance contained therein is controlled by or determined by the device itself and not the environment of use.

By "substantially continuous" as used in, for example, the context of "substantially continuous subcutaneous infusion" or "substantially continuous delivery" is meant to refer to delivery of drug (e.g., sufentanil) in a manner that is substantially uninterrupted for a pre-selected period of drug delivery (other than a period associated with, for example, a bolus injection). Furthermore, "substantially continuous" drug delivery can also encompass delivery of drug at a substantially constant, pre-selected rate or range of rates (e.g., amount of drug per unit time, or volume of drug formulation for a unit time) that is substantially uninterrupted for a pre-selected period of drug delivery.

Pain Susceptible to Management with the Devices and Methods of the Invention

In general, administration of fentanyl or a fentanyl congener according to the invention can be used to facilitate management of pain (e.g., palliative care through, e.g., systemic or centrally mediated analgesia) that is associated with any of a wide variety of disorders, conditions, or diseases. "Pain" as used herein, unless specifically noted otherwise, is meant to encompass pain of any duration and frequency, including, but not limited to, acute pain, chronic pain, intermittent pain, and the like. Causes of pain may be identifiable or unidentifiable. Where identifiable, the origin of pain may be, for example, of malignant, non-malignant, infectious, non-infectious, or autoimmune origin. Of particular interest is the management of pain associated with disorders, diseases, or conditions that require long-term therapy, e.g., chronic and/or persistent diseases or conditions for which therapy involves treatment over a period of several days (e.g., about 3 days to 10 days), to several weeks (e.g., about 2 weeks or 4 weeks to 6 weeks), to several months or years, up to including the remaining lifetime of the subject. Subjects who are not presently suffering from a disease or condition, but who are susceptible to such may also benefit from prophylactic pain management using the devices and methods of the invention, e.g., prior to traumatic surgery. Pain amenable to therapy according to the invention may involve prolonged episodes of pain alternating with pain-free intervals, or substantially unremitting pain that varies in severity.

In general, pain can be nociceptive, somatogenic, neurogenic, or psychogenic. Somatogenic pain can be muscular or skeletal (i.e., osteoarthritis, lumbosacral back pain, posttraumatic, myofascial), visceral (i.e., pancreatitis, ulcer, irritable bowel), ischemic (i.e., arteriosclerosis obliterans), or related to the progression of cancer (e.g., malignant or non-malignant). Neurogenic pain can be due to posttraumatic and postoperative neuralgia, can be related to neuropathies (i.e., diabetes., toxicity, etc.), and can be related to nerve entrapment, facial neuralgia, perineal neuralgia, postamputation, thalamic, causalgia, and reflex sympathetic dystrophy.

Specific examples of conditions, diseases, disorders, and origins of pain amenable to management according to the present invention include, but are not necessarily limited to, cancer pain (e.g., metastatic or non-metastatic cancer), inflammatory disease pain, neuropathic pain, postoperative pain, iatrogenic pain (e.g., pain following invasive procedures or high dose radiation therapy, e.g., involving scar tissue formation resulting in a debilitating compromise of freedom of motion and substantial pain), complex regional pain syndromes, failed-back pain (e.g., acute or chronic back pain), soft tissue pain, joints and bone pain, central pain, injury (e.g., debilitating injuries, e.g., paraplegia, quadriplegia, etc., as well as non-debilitating injury (e.g., to back, neck, spine, joints, legs, arms, hands, feet, etc.)), arthritic pain (e.g., rheumatoid arthritis, osteoarthritis, arthritic symptoms of unknown etiology, etc.), hereditary disease (e.g., sickle cell anemia), infectious disease and resulting syndromes (e.g., Lyme disease, AIDS, etc.), headaches (e.g., migranes), causalgia, hyperesthesia, sympathetic dystrophy, phantom limb syndrome, denervation, and the like. Pain can be associated with any portion(s) of the body, e.g., the musculoskeletal system, visceral organs, skin, nervous system, etc.

Cancer pain is an example of one broad category of pain that can be alleviated according to the methods of the invention. One of the underlying causes of cancer pain is the severe local stretching of tissues by the neoplastic lesion. For example, as the cancer cells proliferate in an unrestricted manner, the tissues in the local region of cancer cell proliferation are subjected to mechanical stress required to displace tissue and accommodate the increased volume occupied by the tumor mass. When the tumor burden is confined to a small enclosed compartment, such as the marrow of a bone, the resulting pressure can result in severe pain. Another cause of cancer pain can result from the aggressive therapies used to combat the patient's cancer, e.g., radiation therapy, chemotherapy, etc. Such cancer therapies can involve localized or widespread tissue damage, resulting in pain.

Pain associated with any type of malignant or non-malignant cancer is amenable to alleviation according to the invention. Specific examples of cancers that can be associated with pain (due to the nature of the cancer itself or therapy to treat the cancer) include, but are not necessarily limited to lung cancer, bladder cancer, melanoma, bone cancer, multiple myeloma, brain cancer, non-Hodgkins lymphoma, breast cancer, oral cancers, cervical cancer, ovarian cancer, colon cancer, rectal cancer, pancreatic cancer, dysplastic nevi, endocrine cancer, prostate cancer, head and neck cancers, sarcoma, Hodgkins disease, skin cancer, kidney cancer, stomach cancer, leukemia, testicular cancer, liver cancer, uterine cancer, and aplastic anemia. Certain types of neuropathic pain can also be amenable to treatment according to the invention.

Back pain, which is also amenable to management using the methods of the invention, is another broad category of pain that can be alleviated by application of the methods of the invention. Back pain is generally due to one or more of the following six causes: (i) stress on intervertebral facet joints, caused by slippage, arthritis, wedging, or scoliosis; (ii) radiculopathy, the mechanical compression of the nerve root due to bulging discs or tumors; (iii) tendonitis or tendon sprain; (iv) muscle spasm or muscle sprain; (v) ischemia, a local insufficiency in circulatory flow; and (vi) neuropathy, damage to nervous tissue of metabolic etiology or arising from cord tumors or central nervous system disease.

The methods of the invention can be used to manage pain in patients who are opioid naive or who are no longer opioid naive, although due to the potency of the drugs administered, patients are preferably not opioid naive. Exemplary opioid naive patients are those who have not received long-term opioid therapy for pain management. Exemplary non-opioid naive patients are those who have received short-term or long-term opioid therapy and have developed tolerance, dependence, or other undesirable side effect. For example, patients who have intractable adverse side effects with oral, intravenous, or intrathecal morphine, transdermal fentanyl patches, or conventionally administered subcutaneous infusions of fentanyl, morphine or other opioid can achieve good analgesia and maintain favorable side-effects profiles with delivery of fentanyl or a fentanyl congener when administered in the dose ranges and/or low volume rates described above.

Fentanyl and Fentanyl Congeners and Formulations

Fentanyl, congeners of fentanyl, and specific derivatives or analogs of fentanyl (e.g., other derivatives, particularly 4-anilidopiperidine derivatives of morphine) are contemplated for delivery according to the invention, although variations within the scope of the invention will be readily apparent to the ordinarily skilled artisan upon reading the disclosure provided herein. Exemplary fentanyl congeners include, but are not necessarily limited to sufentanil, alfentanil, lofentanil, carfentanil, remifentanil, trefentanil, and mirfentanil.

The specific fentanyl congener used can vary with a variety of factors, including the type of pain to be alleviated, the patient's tolerance and/or previous exposure to opioids, etc. The relative potency of fentanyl or the fentanyl congener may also be considered in selection of the drug to be delivered. For example, the rank order of potency of fentanyl and selected fentanyl congeners relative to morphine is as follows: morphine<alfentanil<fentanyl<sufentanil<lofentanil<carfentanil. Fentanyl is estimated to be 292 times, sufentanil, 4,521 times, lofentanil 5,440 times, and carfentanil 9,441 times more potent than morphine. For a review of the pharmacokinetics of sufentanil, fentanyl, and other fentanyl congeners, see, e.g., Meert (1996) *Pharm. World Sci.* 18:1–15; Scholz et al. 1996 *Clin. Pharmacokinet.* 31:275–92.

In a preferred embodiment, the drug is the fentanyl congener sufentanil. Sufentanil is preferred because it exhibits an appropriate potency, has been previously administered according to conventional methods, has a wide therapeutic index (see Meert (1996) *Pharm. World Sci.* 18:1–15), exhibits good stability, and provides for reduced side effects when delivered according to the methods of the invention. Furthermore, the inventors have found that the lipophilicity of sufentanil is particularly suitable for subcutaneous delivery.

Methods for manufacture of fentanyl, sufentanil and other fentanyl congeners are well known in the art, see, e.g., sufentanil (e.g., U.S. Pat. No. 3,998,834; chemical name: ((N-[4-(methyoxymethyl)-1-[2-(2-thienyl)ethyl]-4-piperidinyl]-N-phenylpropanamide 2-hydroxy-1,2,3,-propanetricarboxylate (1:1); $C_{22}H_{30}N_2O_2S$), fentanyl (e.g., U.S. Pat. No. 3,141,823; chemical name: N-phenyl-N-[1-(2-phenylethyl)-4-piperidinyl]propanamide), alfentanil (e.g., U.S. Pat. No. 4,167,574; chemical name: N-[1-[2-(4-ethyl-4,5-dihydro-5-oxo-1H-tetrazol -1-yl)ethyl]-4-(methoxymethyl) -4-piperidinyl]-N-phenylpropanamide ($C_{21}H_{32}N_6O_3$)), lofenatnil (e.g., U.S. Pat. No. 3,998,834; chemical name: 3-methyl-4-[(1-oxopropyl)phenylamino]-1-(2-phenylethyl)4-piperidinecarboxylic acid methyl ester), carfentanil (chemical name: methyl-4-[(1-oxopropyl)phenylamino]-1-(2-phenylethyl)-4-piperidinecarboxylate ($C_{24}H_{30}N_2O_3$)), remifentanil (chemical name: 3-[4-methoxycarbonyl-4-[(1-oxopropyl) phenylamino]1-piperidine]propanoic acid), trefentanil (chemical name: N-(1-(2-(4-ethyl-4,5-dihydro-5-oxo-1H-tetrazol-1-yl)ethyl)-4-phenyl-4-piperidinyl)-N-(2-fluorophenyl)-propanamide, and mirfentanil (chemical name: [N-(2-pyrazinyl)-N-(1-phenethyl4-piperidinyl)-2-furamide).

Fentanyl and fentanyl congeners are discussed in detail in, for example, Goodman and Gilman's The Pharmacological Basis of Therapeutics, Chapter 23, "Opioid Analgesics and Antagonists", pp. 521–555 ($9^{th}$ Ed. 1996); Baly et al. 1991 *Med Res. Rev.* 11:403–36 (evolution of the 4-anilidopiperidine opioids); and Feldman et al. 1991 *J. Med. Chem.* 34:2202–8 (design, synthesis, and pharmacological evaluation of opioid analgesics). For additional information on fentanyl and fentanyl congeners, see, e.g., Scholz et al. 1996 *Clin. Pharmacokinet.* 31:275–92 (clinical pharmacokinetics of alfentanil, fentanyl, and sufentanil);

Meert 1996 *Pharmacy World Sci.* 18:1–15 (describing pharmacotherapy of morphine, fentanyl, and fentanyl congeners); Lemmens et al. 1995 *Anesth. Analg.* 80:1206–11 (pharmacokinetics of mirfentanil); Minto et al., 1997 *Int. Anesthesiol. Clin.* 35:49–65 (review of recently developed opioid analgesics); James 1994 *Expert Opin. Invest. Drugs* 3:331–40 (discussion of remifentanil); Rosow 1993 *Anesthesiology* 79:875–6 (discussion of remifentanil); Glass 1995 *Eur. J. Anaesthesiol.* Suppl. 10:73–4. (pharmacology of remifentanil); and Lemmens et al. 1994 *Clin. Pharmacol. Ther.*56:261–71 (pharmacokinetics of trefentanil).

Fentanyl or a fentanyl congener can be provided in the formulation as the opioid base and/or the opioid pharmaceutically acceptable salt. The pharmaceutically acceptable salt embraces the inorganic and the organic salt. Representative salts include a member selected from the group consisting of hydrobromide, hydrochloride, mutate, citrate, succinate, n-oxide, sulfate, malonate, acetate, phosphate dibasic, phosphate monobasic, acetate trihydrate, bi(heplafluorobutyrate), maleate, bi(methylcarbamate), bi(pentafluoropropionate), mesylate; bi(pyridine-3-carboxylate), bi(trifluoroacetate), bitartrate, chlorhydrate, fumarate and sulfate pentahydrate.

Fentanyl or a fentanyl congener can be provided in any of a variety of formulations compatible with parenteral delivery, provided that such formulation is stable (i.e., not subject to degradation to an unacceptable amount at body temperature). The concentration of fentanyl or fentanyl congener in the formulation may vary. from about 0.1 wt. % to about 50 or 75 wt %. The drug can be provided in any form suitable to be carried by the controlled drug delivery device and released parenterally for systemic distribution, e.g., solid, semi-solid, gel, liquid, suspension, emulsion, osmotic dosage formulation, diffusion dosage formulation, erodible formulation, etc. Of particular interest is the administration of sufentanil in an form suitable for administration using an implanted pump, e.g., an osmotic pump.

In one embodiment, the fentanyl or fentanyl congener is present in the formulation in a concentration substantially higher than conventional formulations, e.g., current commercially available formulations. By "substantially higher," it is intended that the fentanyl or fentanyl congener is present in the formulation in a concentration of at least about 2, at least about 5, at least about 10, at least about 20, at least about 50, at least about 100, at least about 250, at least about 500, at least about 1000, at least about 1500, at least about 2000, at least about 2500, at least about 3000, at least about 3500, at least about 4000, at least about 5000, at least about 6000, at least about 7000, at least about 8000, at least about 9000, at least about 10,000 times, or greater, than the solubility of fentanyl or fentanyl congener in aqueous solution.

Formulations of the invention comprise fentanyl or a fentanyl congener in a concentration of at least about 0.5 mg/mL, 1 mg/mL, 10 mg/mL, 25 mg/mL, 50 mg/mL, 75 mg/mL, 100 mg/mL, 150 mg/mL, 200 mg/mL, 225 mg/mL, 250 mg/mL, 300 mg/mL, 350 mg/mL, 400 mg/mL, 450 mg/mL, 500 mg/mL, or greater. Formulations of the invention comprising fentanyl or fentanyl congener are in solution, e.g., are dissolved in a liquid.

Pharmaceutical grade organic or inorganic carriers and/or diluents suitable for systemic delivery can be included in the formulations suitable for delivery according to the invention. Such physiologically acceptable carriers are well known in the art. Exemplary liquid carriers for use in accordance with the present invention can be sterile non-aqueous or aqueous solutions which contain no materials other than the active ingredient. In general, hydrophobic solvents are generally preferred due to the lipophilicity of fentanyl and fentanyl congeners. The formulations can optionally further comprise a buffer such as sodiumphosphate at physiological pH value, physiological saline or both (i.e., phosphate-buffered saline). Suitable aqueous carriers may optionally further comprise more than one buffer salt, as well as other salts (such as sodium and potassium chlorides) and/or other solutes.

In some exemplary embodiments, the formulation comprises fentanyl or a fentanyl congener (generally as a base) and a low molecular weight (e.g., MW less than about 300 g/mol) alcohol. In these embodiments, the fentanyl or fentanyl congener is present in the formulation in a concentration of from about 0.5 mg/mL to about 500 mg/mL, from about 1 mg/mL to about 450 mg/mL, from about 50 mg/mL to about 400 mg/mL, from about 75 mg/mL to about 300 mg/mL, or from about 100 mg/mL to about 250 mg/mL. Suitable low molecular weight alcohols include those which are pharmaceutically acceptable, and which preferably comprise an aromatic moiety, and which are relatively immiscible in water (e.g., less than about 5, less than about 4, less than about 3, less than about 2, less than about 1 gram can dissolve in 25 ml $H_2O$), including, but not limited to, benzyl alcohol, and derivatives thereof. Small amounts of other pharmaceutically acceptable substances such as other pharmaceutically acceptable alcohols, e.g., ethanol, or water, may also be present, and, if present, are present in an amount of less than about 10%, less than about 5%, or less than about 1%. In a particular embodiment, the formulation comprises fentanyl or fentanyl congener, with sufentanil being of particular interest, in 100% benzyl alcohol.

In additional exemplary embodiments, the formulation comprises fentanyl or a fentanyl congener (generally as a base), and a nonionic surfactant, in an alcohol ester, e.g., an ester of a low molecular weight alcohol as described above. In these embodiments, the fentanyl or fentanyl congener is present in the formulation in a concentration of from about 0.5 mg/ml or 1 mg/mL to about 500 mg/mL, from about 50 mg/mL to about 300 mg/mL, from about 75 mg/mL to about 275 mg/mL, or from about 100 mg/mL to about 250 mg/mL. Suitable alcohol esters include those which are pharmaceutically acceptable, which preferably comprise an aromatic moiety, and which are insoluble in water, including, but not limited to, benzyl benzoate, and derivatives thereof. Small amounts of pharmaceutically acceptable substances such as pharmaceutically acceptable alcohols or other pharmaceutically acceptable alcohol esters, or water, may also be present, and, if present, are present in an amount of less than about 10%, less than about 5%, or less than about 1%. In a particular embodiment, the alcohol ester is 100% benzyl benzoate, with sufentanil as the fentanyl congener being of particular interest.

Suitable nonionic surfactants include those which are pharmaceutically acceptable, including but not limited to, polysorbate, e.g., polysorbate 20, polysorbate 40, polysorbate 60; sorbitan trioleate; polyoxyethylene polyoxypropyleneglycol, e.g., polyoxyethylene(160)glycol, and polyoxypropylene(30)glycol. Other nonionic surfactants which are suitable for use in the formulations include nonionic surfactants of the fatty acid polyhydroxy alcohol ester type such as sorbitan monolaurate, monooleate, monostearate or monopalmitate, sorbitan tristearate or trioleate, adducts of polyoxyethylene and fatty acid polyhydroxy alcohol esters such as polyoxyethylene sorbitan monolaurate, monooleate, monostearate, monopalmitate, tristearate or trioleate, polyethylene glycol fatty acid esters such as polyoxyethyl stearate, polyethylene glycol 400 stearate, polyethylene glycol 2000 stearate, in particular ethylene oxide-propylene oxide block copolymers of the Pluronics (Wyandotte) or Synperonic (ICI). In particular embodiments, the nonionic surfactant is polysorbate 20, polysorbate 40, polysorbate 60, or sorbitan trioleate, or mixtures of one or more of the foregoing.

In general, a nonionic surfactant is present in the formulation in a concentration of from about 50 mg/mL to about 200 mg/mL, from about 75 mg/mL to about 175 mg/mL, or from about 100 mg/mL to about 150 mg/mL. In a particular embodiment, the nonionic surfactant is present in the formulation at 100 mg/mL.

Formulations of particular interest for delivery are characterized in that the fentanyl or fentanyl congener is present in a high concentration, as described above. The fentanyl or fentanyl congener is soluble in the formulation, i.e., little or no fentanyl or fentanyl congener precipitates are present, and further, little or no fentanyl or fentanyl congener precipitates form when the formulation comes in contact with an aqueous environment such as a body fluid. Precipitates of fentanyl or fentanyl congeners, when present at all, are present in the formulation at less than about 10%, less than about 7.5%, less than about 5%, less than about 2.5%, less than about 1%, or less than about 0.1% by weight of the total fentanyl or fentanyl congener present in the formulation. Whether precipitates have formed can be determined using any method known in the art, including, but not limited to, visual inspection with the unaided eye, or under low (e.g., 10×or 25×) magnification.

The formulations comprising fentanyl or a fentanyl congener and suitable for administration according to the invention may comprise additional active or inert components that are pharmaceutically acceptable and compatible with the active ingredient. Suitable excipients can comprise dextrose, glycerol, alcohol (e.g., ethanol), and the like, and combinations of one or more thereof with vegetable oils, propylene glycol, polyethylene glycol, benzyl alcohol, benzyl benzoate, dimethyl sulfoxide (DMSO), organics, and the like to provide a suitable composition. In addition, if desired, the composition can comprise hydrophobic or aqueous surfactants, dispersing agents, wetting or emulsifying agents, isotonic agents, pH buffering agents, dissolution promoting agents, stabilizers, antiseptic agents and other typical auxiliary additives employed in the formulation of pharmaceutical preparations.

Exemplary additional active ingredients that can be present in the formulations useful with the invention can include an opioid antagonist (e.g., to further decrease the possibility of addiction, or dependence, see, e.g., an exemplary osmotic dosage formulation comprising an opioid agonist and an opioid antagonist is described in U.S. Pat. No. 5,866,164.

Implantation and Delivery Sites

The drug delivery device can be implanted at any suitable implantation site using methods and devices well known in the art. As noted infra, an implantation site is a site within the body of a subject at which a drug delivery device is introduced and positioned. Implantation sites include, but are not necessarily limited to a subdermal, subcutaneous, intramuscular, or other suitable site within a subject's body. Subcutaneous implantation sites are preferred because of convenience in implantation and removal of the drug delivery device. In some embodiments, the implantation site is at or near the delivery site (e.g., the delivery site is not distant from the implantation site), and thus should be a site compatible with systemic delivery of drug (e.g., a subcutaneous site). Where the implantation site and the delivery site are distant, then it is not necessary that the implantation site be a site compatible with systemic delivery of drug. For example, the drug delivery device can be implanted at a subcutaneous site, and the delivery site can be an intravenous or other site suitable for systemic delivery of drug. Delivery of drug from a drug delivery device at an implantation site that is distant from a delivery site can be accomplished by providing the drug delivery device with a catheter, as described in more detail below.

The delivery site is an area of the body to which drug is delivered for entry into the systemic circulation, i.e., a site which allows systemic access of the drug. Delivery sites include, but are not necessarily limited to, subcutaneous, intravenous, intra-arterial, intra-muscular, intra-adipose tissue, intra-lymphatic and sublingual sites. Subcutaneous delivery sites are of particular interest in the present application. Exemplary subcutaneous delivery sites include external subcutaneous sites (e.g., under the skin of the arm, shoulder, neck, back, or leg) and internal subcutaneous sites within a body cavity (e.g., within the mouth). Delivery to a subcutaneous site further enhances these advantages of the invention, since delivery to a subcutaneous site involves the greatest contact with tissue that can readily absorb the drug. Furthermore, the present invention treats pain by delivery of fentanyl or its congeners (e.g., sufentanil), which drugs are lipophilic. The lipophilicity of these drugs further enhances their absorption at a delivery site, particularly at a subcutaneous delivery site.

Delivery of Fentanyl or Fentanyl Congeners

In general, the formulation of fentanyl or fentanyl congener is delivered at a volume rate that is compatible with the delivery site, and at a dose that is therapeutically effective in reduction of pain (e.g., sufficient to accomplish substantial management of pain) while reducing the presence or risk of side effects that can be associated with administration of opioid drugs.

Subjects suffering from or susceptible to pain can receive alleviation of pain according to the method of the invention for any desired period of time. In general, administration of fentanyl or fentanyl congener according to the invention can be sustained for several hours (e.g., 2 hours, 12 hours, or 24 hours to 48 hours or more), to several days (e.g., 2 to 5 days or more), to several months or years. Typically, delivery can be continued for a period ranging from about 1 month to about 12 months or more. The fentanyl or fentanyl congener may be administered to an individual for a period of, for example, from about 2 hours to about 72 hours, from about 4 hours to about 36 hours, from about 12 hours to about 24 hours, from about 2 days to about 30 days, from about 5 days to about 20 days, from about 7 days or more, from about 10 days or more, from about 100 days or more, from about 1 week to about 4 weeks, from about 1 month to about 24 months, from about 2 months to about 12 months, from about 3 months to about 9 months, from about 1 month or more, from about 2 months or more, or from about 6 months or more; or other ranges of time, including incremental ranges, within these ranges, as needed. This extended period of opioid delivery is made possible by the ability of the invention to provide both adequate pain relief, while minimizing the severity of opioid side effects (e.g., nausea, vomiting, sedation, confusion, respiratory depression, etc.). In particular embodiments, the fentanyl or fentanyl congener is delivered to the subject without the need for re-accessing the device and/or without the need for re-filling the device. In these embodiments, high-concentration formulations of fentanyl or fentanyl congener are of particular interest.

Preferably, delivery of fentanyl or fentanyl congener is in a patterned fashion, more preferably in a substantially continuous fashion, e.g., substantially uninterrupted for a preselected period of drug delivery, and more preferably at a substantially constant, pre-selected rate or range of rates (e.g., amount of drug per unit time, or volume of drug formulation for a unit time). The drug is preferably delivered at a low volume rate of from about 0.01 µl/day to about 2 ml/day, preferably about 0.04 µl/day to about 1 ml/day, generally about 0.2 µl/day to about 0.5 ml/day, typically from about 2.0 µl/day to about 0.25 ml/day.

Systemic administration of drug by delivery using an implanted pump according to the invention is particularly preferred where delivery by other routes has become undesirable, e.g., the subject has experienced intractable adverse side effects with oral, intravenous, or intrathecal morphine, transdermal fentanyl patches, or conventionally administered subcutaneous infusions (e.g., using a syringe driver system or other delivery system that requires relatively high volume delivery). Delivery using an implanted pump is convenient for the subject, as the implantation and removal procedures are simple and can be conducted on an out-patient basis where the patient's health allows such. Subcutaneously implanted drug delivery devices also increase patient compliance, prevent drug diversion and abuse, reduce the risk of infection associated with external pumps or other methods that require repeated breaking of the skin and/or maintenance of a port for administration.

Delivery of drug to a subcutaneous site at a low volume rate is a particularly preferred embodiment of the invention. In general, low volume rate drug delivery avoids accumulation of drug at the delivery site (e.g., depot or pooling effect) by providing for a rate of administration that is less than, the same as, or only very slightly greater than the rate of removal of drug from the delivery site (e.g., by absorption of drug in tissues at the site, movement of drug away from the site by flow of blood or other bodily fluids, etc.). Thus, in addition to providing an implantable system for delivery of highly potent drugs such as fentanyl and fentanyl congeners (e.g., sufentanil), the present invention also provides a method for treating pain by elegantly balancing the rates of drug absorption and drug delivery to accomplish administration of a therapeutically effective amount of drug, while avoiding accumulation of drug at the delivery site.

In one embodiment, a drug delivery device provides for substantially continuous, subcutaneous delivery of drug at a preselected rate. For example, for subcutaneous delivery of sufentanil, the drug can be delivered at a rate of from about 0.01 µg/hr to about 200 µg/hr, usually from about 0.01 µg/hr, 0.25 µg/hr, or 3 µg/hr to about 85 µg/hr, and typically between about 5 µg/hr to about 100 µg/hr. In a specific exemplary embodiment, sufentanil is delivered at a rate of from about 0.01 µg/hr, 0.1 µg/hr, 0.25 µg/hr, 1 µg/hr, generally up to about 200 µg/hr. Appropriate amounts of fentanyl or fentanyl congener can be readily determined by the ordinarily skilled artisan based upon, for example, the relative potency of these drugs. The actual dose of drug delivered will vary with a variety of factors such as the potency and other properties of the selected drug used (e.g., lipophilicity, etc.).

Drug Delivery Devices for use in the Invention

Any of a variety of controlled drug delivery devices can be used in the present invention to accomplish delivery of a drug formulation comprising fentanyl or fentanyl congener. In general, the drug delivery device minimally comprises a controlled drug delivery device and, in one embodiment, further comprises and a drug delivery catheter, e.g., where the implantation site is distant from the delivery site.

Drug delivery devices suitable for use with the present invention can take advantage of any of a variety of controlled drug release devices. In general, the drug release devices suitable for use in the invention comprise a drug reservoir for retaining a drug formulation or alternatively some substrate or matrix which can hold drug (e.g., polymer, binding solid, etc.). The drug release device can be selected from any of a variety of implantable controlled drug delivery system known in the art. Controlled drug release devices suitable for use in the present invention generally can provide for delivery of the drug from the device at a selected or otherwise patterned amount and/or rate to a selected site in the subject.

In some embodiments, the delivery device is one that is adapted for delivery of fentanyl or fentanyl congener over extended periods of time. Such delivery devices may be adapted for administration of fentanyl or fentanyl congener for several hours (e.g., 2 hours, 12 hours, or 24 hours to 48 hours or more), to several days (e.g., 2 to 5 days or more, from about 100 days or more), to several months or years. In some of these embodiments, the device is adapted for delivery for a period ranging from about 1 month to about 12 months or more. The drug delivery device may be one that is adapted to administer fentanyl or fentanyl congener to an individual for a period of, for example, from about 2 hours to about 72 hours, from about 4 hours to about 36 hours, from about 12 hours to about 24 hours, from about 2 days to about 30 days, from about 5 days to about 20 days, from about 7 days or more, from about 10 days or more, from about 100 days or more; from about 1 week to about 4 weeks, from about 1 month to about 24 months, from about 2 months to about 12 months, from about 3 months to about 9 months, from about 1 month or more, from about 2 months or more, or from about 6 months or more; or other ranges of time, including incremental ranges, within these ranges, as needed. In these embodiments, high-concentration formulations of fentanyl or fentanyl congener described herein are of particular interest for use in the invention.

Release of drug from the device, particularly controlled release of drug, can be accomplished in any of a variety of ways according to methods well known in the art, e.g., by incorporation of drug into a polymer that provides for substantially controlled diffusion of drug from within the polymer, incorporation of drug in a biodegradable polymer, providing for delivery of drug from an osmotically-driven device, etc. Where the drug delivery device comprises a drug delivery catheter, drug can be delivered through the drug delivery catheter to the delivery site as a result of capillary action, as a result of pressure generated from the drug release device, by diffusion, by electrodiffusion or by electroosmosis through the device and/or the catheter.

The drug delivery device must be capable of carrying the drug formulation in such quantities and concentration as therapeutically required, and must provide sufficient protection to the formulation from attack by body processes for the duration of implantation and delivery. The exterior is thus preferably made of a material that has properties to diminish the risk of leakage, cracking, breakage, or distortion so as to prevent expelling of its contents in an uncontrolled manner under stresses it would be subjected to during use, e.g., due to physical forces exerted upon the drug release device as a result of movement by the subject or physical forces associated with pressure generated within the reservoir associated with drug delivery. The drug reservoir or other means for holding or containing the drug must also be of such material as to avoid unintended reactions with the active agent formulation, and is preferably biocompatible (e.g., where the device is implanted, it is substantially non-reactive with respect to a subject's body or body fluids).

Suitable materials for the reservoir or drug holding means for use in the delivery devices of the invention are well known in the art. For example, the reservoir material may comprise a non-reactive polymer or a biocompatible metal or alloy. Suitable polymers include, but are not necessarily limited to, acrylonitrile polymers such as acrylonitrile-butadiene-styrene polymer, and the like; halogenated polymers such as polytetrafluoroethylene, polyurethane, polychlorotrifluoroethylene, copolymer tetrafluoroethylene and hexafluoropropylene; polyethylene vinylacetate (EVA), polyimide; polysulfone; polycarbonate; polyethylene; polypropylene; polyvinylchloride-acrylic copolymer; polycarbonate-acrylonitrile-butadiene-styrene; polystyrene; cellulosic polymers; and the like. Further exemplary polymers are described in The Handbook of Common Polymers, Scott and Roff, CRC Press, Cleveland Rubber Co., Cleveland, Ohio.

Metallic materials suitable for use in the reservoir of the drug release device include stainless steel, titanium, platinum, tantalum, gold and their alloys; gold-plated ferrous alloys; platinum-plated titanium, stainless steel, tantalum, gold and their alloys as well as other ferrous alloys; cobalt-chromium alloys; and titanium nitride-coated stainless steel, titanium, platinum, tantalum, gold, and their alloys.

Exemplary materials for use in polymeric matrices include, but are not necessarily limited to, biocompatible polymers, including biostable polymers and biodegradable polymers. Exemplary biostable polymers include, but are not necessarily limited to silicone, polyurethane, polyether urethane, polyether urethane urea, polyamide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-a-chloro-p-xylene, polymethylpentene, polysulfone and other related biostable polymers. Exemplary biodegradable polymers include, but are not necessarily limited to, polyanhydrides, cyclodestrans, polylacticglycolic acid, polyorthoesters, n-vinyl alcohol, polyethylene oxide/polyethylene terephthalate, polyglycolic acid, polylactic acid and other related bioabsorbable polymers.

Where the drug formulation is stored in a reservoir comprising metal or a metal alloy, particularly titanium or a titanium alloy having greater than 60%, often greater than 85% titanium is preferred for the most size-critical applications, for high payload capability and for long duration applications and for those applications where the formulation is sensitive to body chemistry at the implantation site or where the body is sensitive to the formulation. Most preferably, the drug delivery devices are designed for storage with drug at room temperature or higher.

Drug release devices suitable for use in the invention may be based on any of a variety of modes of operation. For example, the drug release device can be based upon a diffusive system, a convective system, or an erodible system (e.g., an erosion-based system). For example, the drug release device can be an osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump, can also be suitable for use with the present invention. Examples of such devices include those described in, for example, U.S. Pat. Nos. 4,692,147; 4,360,019; 4,487,603; 4,360,019; 4,725,852, and the like. In general, the present methods of drug delivery can be accomplished using any of a variety of refillable, non-exchangeable pump systems. Pumps and other convective systems are generally preferred due to their generally more consistent, controlled release over time. Osmotic pumps are particularly preferred due to their combined advantages of more consistent controlled release and relatively small size. Of the osmotic pumps, the DUROST™ osmotic pump is particularly preferred (see, e.g., WO 97/27840 and U.S. Pat. Nos. 5,985,305 and 5,728,396)).

In one embodiment, the drug release device is a controlled drug release device in the form of an osmotically-driven device. Preferred osmotically-driven drug release systems are those that can provide for release of drug in a range of rates of from about 0.01 $\mu$g/hr to about 200 $\mu$g/hr, and which can be delivered at a volume rate of from about 0.01 $\mu$l/day to about 100 $\mu$l/day (i.e., from about 0.0004 $\mu$l/hr to about 4 $\mu$l/hr), preferably from about 0.04 $\mu$l/day to about 10 $\mu$l/day, generally from about 0.2 $\mu$l/day to about 5 $\mu$l/day, typically from about 0.5 $\mu$l/day to about 1 $\mu$l/day. In one embodiment, the volume/time delivery rate is substantially constant (e.g., delivery is generally at a rate ± about 5% to 10% of the cited volume over the cited time period, e.g., a volume rate of about.

In general, the drug delivery devices suitable for use in the invention are those that can deliver drug at a low dose, e.g., for sufentanil from about 0.01 $\mu$g/hr to about 200 $\mu$g/hr, and preferably at a low volume rate e.g., on the order of nanoliters to microliters per day. In one embodiment, a volume rate of from about 0.01 $\mu$l/day to about 2 ml/day is accomplished by delivery of about 80 $\mu$l/hour over a period of 24 hours, with the delivery rate over that 24 hours period fluctuating over that period by about ±5% to 10%. Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

Delivery of Fentanyl or Fentanyl Congener Using a Drug Delivery Device Comprising a Drug Delivery Catheter In some embodiments it may be desirable to provide a drug delivery catheter with the drug delivery device, e.g., where the implantation site and the desired delivery site are not the same or adjacent. The drug delivery catheter is generally a substantially hollow elongate member having a first end (or "proximal" end) associated with the drug release device of the drug delivery device, and a second end (or "distal" end) for delivery of the drug-comprising formulation to a desired delivery site. Where a drug delivery catheter is used, a first end of the drug delivery catheter is associated with or attached to the drug delivery device so that the lumen of the drug delivery catheter is in communication with the drug reservoir in the drug delivery device, so that a formulation contained in a drug reservoir can move into the drug delivery catheter, and out a delivery outlet of the catheter which is positioned at the desired delivery site.

The body of the catheter defines a lumen, which lumen is to have a diameter compatible with providing leak-proof delivery of drug formulation from the drug delivery device.

Where the drug delivery device dispenses drug by convection (as in, e.g., osmotic drug delivery systems), the size of the catheter lumen leading from the reservoir of the drug release system can be designed as described by Theeuwes (1975) *J. Pharm. Sci.* 64:1987–91.

The body of the catheter can be of any of a variety of dimensions and geometries (e.g., curved, substantially straight, tapered, etc.), that can be selected according to their suitability for the intended site for drug delivery. The distal end of the drug delivery catheter can provide a distinct opening for delivery of drug, or as a series of openings.

The drug delivery catheter may be produced from any of a variety of suitable materials, and may be manufactured from the same or different material as the reservoir of the drug release device. Impermeable materials suitable for use in production of the controlled drug release device as described above are generally suitable for use in the production of the drug delivery catheter. Exemplary materials from which the drug delivery catheter can be manufactured include, but are not necessarily limited to, polymers; metals; glasses; polyolefins (high density polyethylene (HDPE), low density polyethylene (LDPE), linear low density polyethylene (LLDPE), polypropylene (PP), and the like); nylons; polyethylene terephtholate; silicones; urethanes; liquid crystal polymers; PEBAX®; HYTREL®; TEFLON®; perflouroethylene (PFE) perflouroalkoxy resins (PFA); poly(methyl methacrylate) (PMMA); multilaminates of polymer, metals, and/or glass; nitinol; and the like.

The drug delivery catheter can comprise additional materials or agents (e.g., coatings on the external or internal catheter body surface(s)) to facilitate placement of the drug delivery catheter and/or to provide other desirable characteristics to the catheter. For example, the drug delivery catheter inner and/or outer walls can be coated with silver or otherwise coated or treated with antimicrobial agents, thus further reducing the risk of infection at the site of implantation and drug delivery.

In one embodiment, the drug delivery catheter is primed with a drug-comprising formulation, e.g., is substantially pre-filled with drug prior to implantation. Priming of the drug delivery catheter reduces delivery start-up time, i.e., time related to movement of the drug from the drug delivery device to the distal end of the drug delivery catheter. This feature is particularly advantageous in the present invention where the drug release device of the drug delivery device releases sufentanil at relatively low flow rates.

FIG. 1 illustrates one embodiment of the invention, wherein fentanyl or a fentanyl congener is delivered from an implanted drug delivery device that provides for sustained, controlled release of fentanyl or fentanyl congener from a drug reservoir to a subcutaneous site. In this example, the drug delivery device 10 is implanted at a subcutaneous site in the patient's arm 5. Flow of drug from the device's drug reservoir and to the subcutaneous site is illustrated by arrows 200. FIG. 2 provides a perspective view of the exemplary drug delivery device 10 implanted in FIG. 1. The drug delivery device 10 comprises proximal and distal ends 11 and 12, with the distal end defining an orifice 15 through which drug exits the drug reservoir 30 for delivery to the subcutaneous site. In the exemplary device 10, controlled release of drug from the reservoir 30 is provided by an osmotic engine comprising a piston 41 and an chamber comprising an osmotic engine 42.

FIG. 3 illustrates an alternative embodiment in which the drug delivery system 100 comprises a drug delivery device 10 and a drug delivery catheter 20. In the example in FIG. 3, the drug release device portion is maintained at a subcutaneous implantation site and the distal end of the drug delivery catheter 20 is implanted at an intravenous delivery site. As shown in the cut-away of the drug delivery device in FIG. 4, the drug delivery system 100 comprises a drug delivery device 10 and a drug delivery catheter 20. The walls of the drug delivery catheter define a lumen, and the drug delivery catheter is associated with the drug delivery device 10 so that a drug delivery pathway is provided from the drug reservoir 30, through orifice 15, and out the distal end 12 of the drug delivery device. The catheter 20 can be positioned for systemic delivery of drug to, for example, vein 7.

Methods for implanting or otherwise positioning drug delivery devices for subcutaneous delivery of a drug are well known in the art. In general, placement of the drug delivery device will be accomplished using methods and tools that are well known in the art, and performed under aseptic conditions with at least some local or general anesthesia administered to the subject: In one embodiment, the drug delivery device is implanted using an implanter such as the device provided in, for example, U.S. Design Pat. No. D402,757; or New Zealand Certificate of Registration of Design No. 29353. Removal and/or replacement of drug delivery devices can also be accomplished using tools and methods that are readily available.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Example 1

Treatment Regimen for Subcutaneous Delivery of Fentanyl or Fentanyl Congener Via DUROS™ Pump 1. Evaluation of Patient The physician first examines the potential patient and evaluates the patient's history to determine if the patient has pain that amenable to treatment by opioids and can safely tolerate such treatment.

2. Selection of Appropriate Dose

If the physician decides to proceed with treatment in accordance with this invention, the physician determines the appropriate dose of drug (e.g., sufentanil) to be administered to the patient. This determination can be performed in a variety of ways. If the patient is already using certain medication to control pain (e.g., oral morphine or the fentanyl transdermal patch), the physician can attempt to correlate the dose of medication previously used by the patient to an appropriate dose of the selected drug (e.g., fentanyl or fentanyl congener such as sufentanil) when infused subcutaneously. This correlation can be made by reference to dose conversion information (e.g., a dose conversion chart) between the previous medication and the selected drug, if such dose conversion information exists. If dose conversion information does not exist for the previous medications and the selected drug, the physician can first switch the patient from the previous medications to another medication for which there exists dose conversion information with the selected drug (e.g., fentanyl or fentanyl congener, e.g., sufentanil).

In the alternative to resorting to dose conversion information, or if such information does not exist, the physician can determine the appropriate dose of drug to treat such patient by infusing the selected drug (e.g., fentanyl or fentanyl congener, e.g., sufentanil) subcutaneously by means of an external pump and adjusting such infusion rates until the proper dose to control the pain with minimal side effects is located.

3. Implantation of DUROS™ Pump

Once the physician has determined the appropriate dose of fentanyl or fentanyl congener (e.g., sufentanil), then the physician selects a DUROS™ Pump containing a formulation comprising the selected drug (e.g., sufentanil) that is capable of delivering the required dosage for up to 3 months. The physician will then implant the DUROS™ Pump into the subcutaneous tissue at the inside of the upper arm of the patient.

4. Treatment of Pain

Once the DUROS™ Pump has become activated by implantation, the formulation of fentanyl or fentanyl congener (e.g., sufentanil) will be delivered systemically to control pain for up to 3 months. Treatment can be stopped prior to the end of such 3 months by explanting the DUROS™ Pump. If treatment is desired beyond 3 months, the expended DUROS™ Pump can be explanted and a replacement DUROS™ Pump may be implanted in the same subcutaneous location.

Example 2

DUROS™ Pump Useful for Delivery of Sufentanil

The following is a description of exemplary drug loading parameters of a DUROS™ osmotic pump used for the delivery of sufentanil. The parameters are based on a nominal fill volume of the pump of 155 μl, with a nominal volumetric delivery rate of 1.4 μl/day for a nominal duration of 110 days (to ensure that a target delivery period of 90 days is achieved). An exemplary DUROS™ pump useful in this protocol is illustrated in FIG. 2, and is approximately 3.76 mm in diameter and 44.21 mm in length.

Example 3

Formulations Comprising Sufentanil in Benzyl Alcohol 397 mg/mL Formulation 3.97 g of sufentanil base were weighed out and added to a portion of benzyl alcohol. The drug was dissolved in the benzyl alcohol by stirring with a magnetic stirrer. When the resultant preparation was clear, additional benzyl alcohol was added to obtain 10 mL of formulation. The resultant formulation concentration was 397 mg/mL.

310 mg/mL Formulation 3.1 g of sufentanil base were weighed out and added to a portion of benzyl alcohol. The drug was dissolved in the benzyl alcohol by stirring with a magnetic stirrer. When the resultant preparation was clear, additional benzyl alcohol was added to obtain 10 mL of formulation. The resultant formulation concentration was 310 mg/mL.

Example 4

Formulations Comprising Sufentanil in Benzyl Benzoate 248 mg/mL Formulation

The vehicle solution was prepared by adding 3 mL of polysorbate 20 to sufficient benzyl benzoate to make 30 mL of solution. The mixture was stirred using a magnetic stirrer until the polysorbate 20 was dispersed in the benzyl benzoate. 7.44 g sufentanil base was weighed out and added to a portion of the vehicle solution. The drug was dissolved by sonicating the flask in a sonication bath. When the resultant preparation was clear, an additional quantity of the vehicle was added to obtain 30 mL of formulation. The resultant formulation concentration was 248 mg/mL.

77 mg/mL Formulation

The vehicle solution was prepared by adding 3 mL of polysorbate 20 to sufficient benzyl benzoate to make 30 mL of solution. The mixture was stirred using a magnetic stirrer until the polysorbate 20 was dispersed in the benzyl benzoate. 2.322 g sufentanil base was weighed out and added to a portion of the vehicle solution. The drug was dissolved by sonicating the flask in a sonication bath. When the resultant preparation was clear, an additional quantity of the vehicle was added to obtain 30 mL of formulation. The resultant formulation concentration was 77.4 mg/mL.

Example 5

Release of Sufentanil from DUROS™ Osmotic Pump

The release of drug from a DUROS™ osmotic pump at

TABLE 1

| | | | Loading Parameters | | | | |
|---|---|---|---|---|---|---|---|
| Dose rate μg/hr | Dose rate μg/day | μg delivered over 110 days | mg delivered over 110 days | Nominal Rate μl/day | Nominal Rate μl/hr | DUROST™ Residence Volume | wt/vol % formulation load |
| 2.5 | 60 | 6600 | 6.6 | 1.4 | 0.058 | 155 | 4.28 |
| 5 | 120 | 10800 | 10.8 | 1.4 | 0.058 | 155 | 8.57 |
| 7.5 | 180 | 16200 | 16.2 | 1.4 | 0.058 | 155 | 12.6 |
| 10 | 240 | 21600 | 21.6 | 1.4 | 0.058 | 155 | 17.1 |
| 20 | 460 | 43200 | 43.2 | 1.4 | 0.058 | 155 | 34.3 |

These parameters thus dictate the amount of drug to be included in the formulation of the pump in order to provide for delivery at the selected dose rate for an approximately 110 day period (e.g., about 3 months).

37° C. was tested in vitro at either 20 μg/hr or 5 μg/hr drug dose rates. Five different systems (five different pumps) were tested for each of the drug delivery rates (20 μg/hr and 5 μg/hr) over a 48 day period.

The release media (RM) is prepared from a phosphate buffered saline (PBS) solution, available commercially as a powder preparation and prepared according to manufacturer's directions. 5% polysorbate 20 was added to the media prior to bringing it to final volume. This solution is the release media (RM). 6 mL of RM was dispensed into a 15 mL conical polypropylene tube, with one tube prepared for each system to be tested. The tubes were placed in a 37° C. water bath and allowed to reach temperature.

A system containing sufentanil is placed into each tube with orifice end down, and completely immersed in the RM. At desired time intervals, the system is removed from the tube using a transfer rod. The system is placed (orifice end down) into a new tube of RM which has been equilibrated in the water bath. An example of time intervals is 0.5 hours, 1, 2, 3, 4, 5, 6, 7, 14, 28, 35 days, continuing weekly until delivery is complete.

In order to determine the amount of sufentanil released, 4 mL of acetonitrile was added to each sample test tube and mixed thoroughly. The sample is then assayed to determine the amount of sufentanil released during the time interval. Sufentanil in the samples was quantitated by HPLC or other methodology capable of quantitating sufentanil in the presence of formulation and RM. The amount released per unit time was calculated for each interval, and a release rate profile prepared by plotting the amount released per unit time on the y-axis against the mean time interval on the x-axis.

Figure 6:
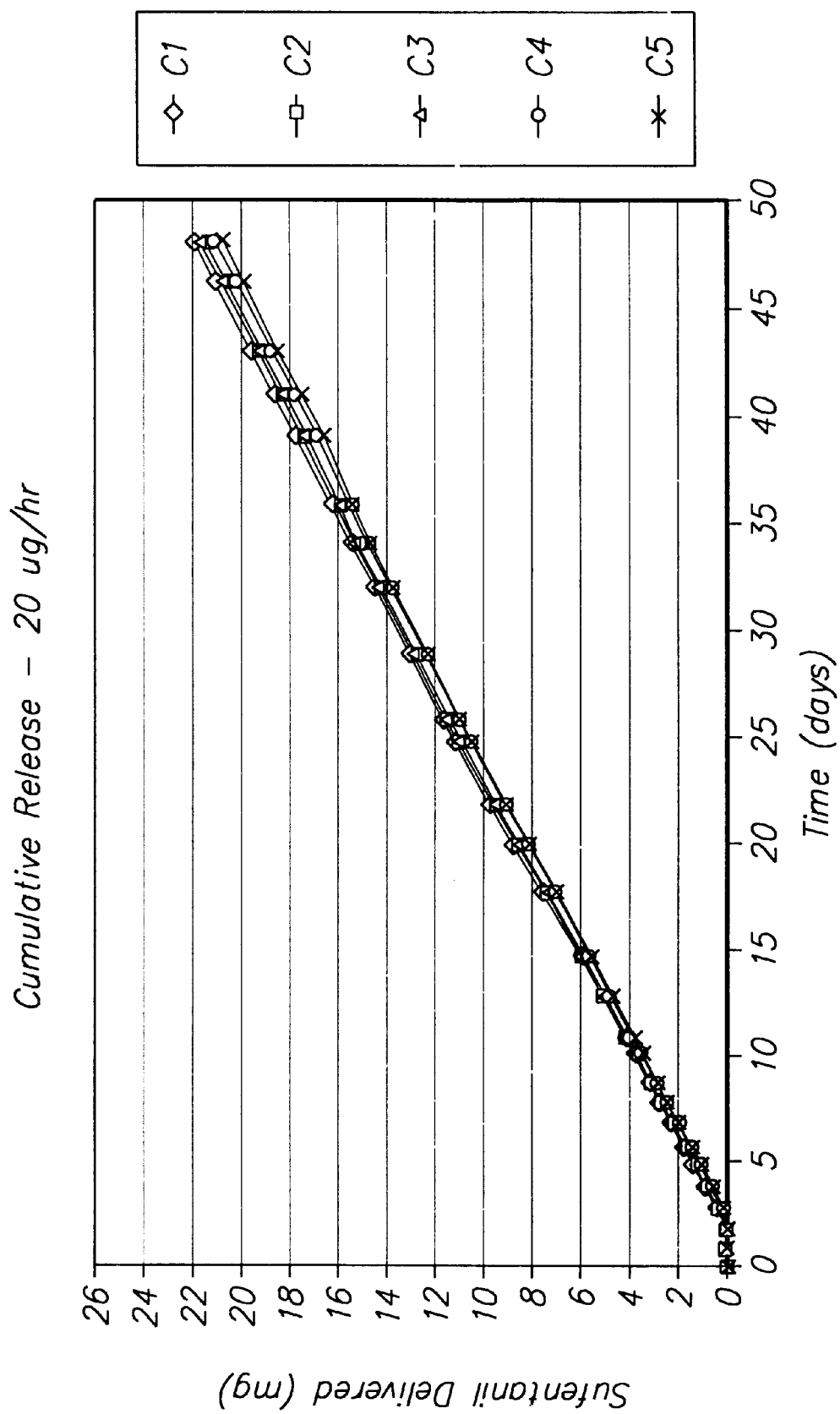
FIG. 6 is a graph showing cumulative release of sufentanil from exemplary osmotic pumps at a rate of 20 µg/hr.
Figure 7:
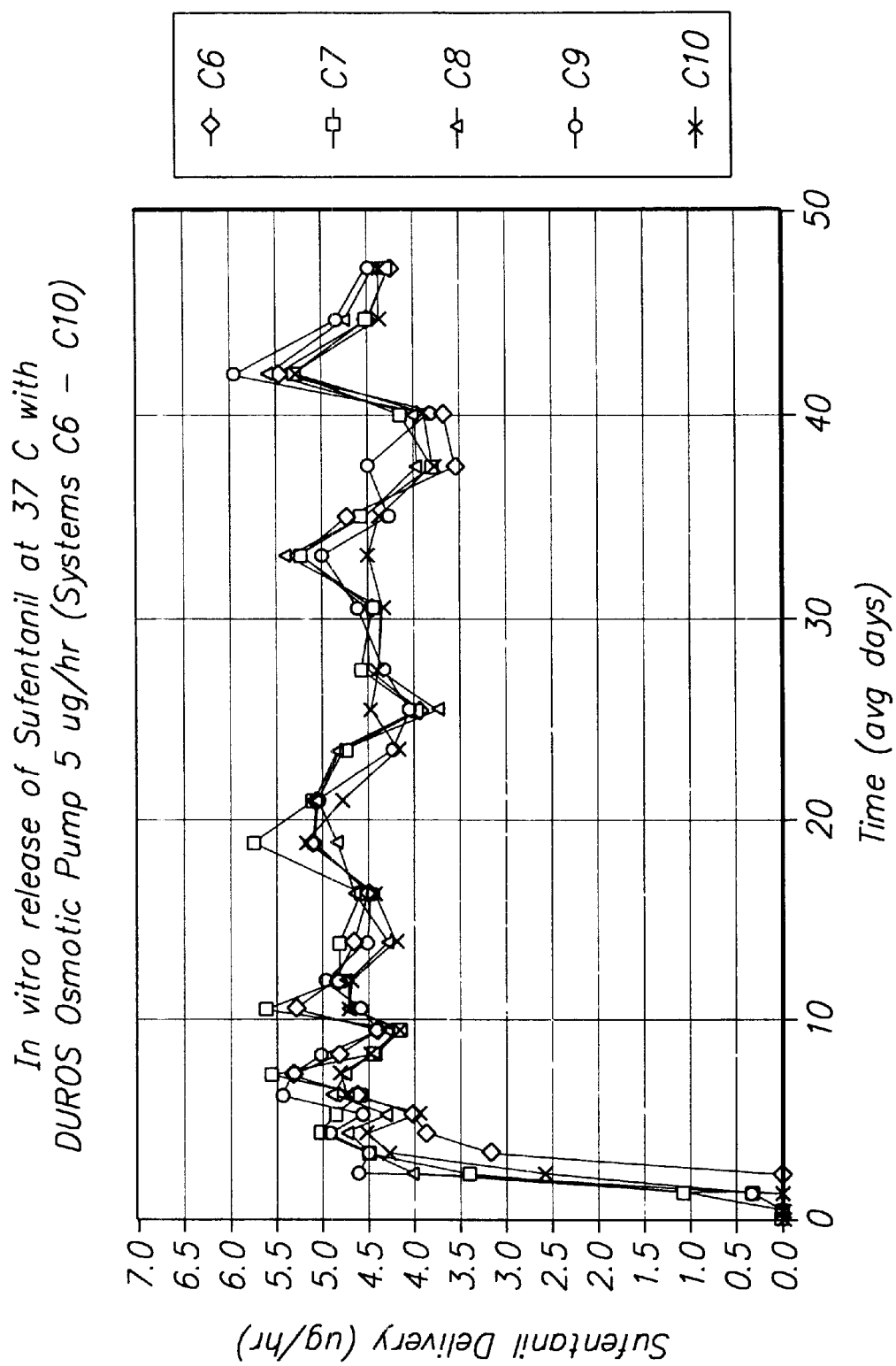
FIG. 7 is a graph showing release of sufentanil from exemplary osmotic pumps at a rate of 5 µg/hr.
Figure 8:
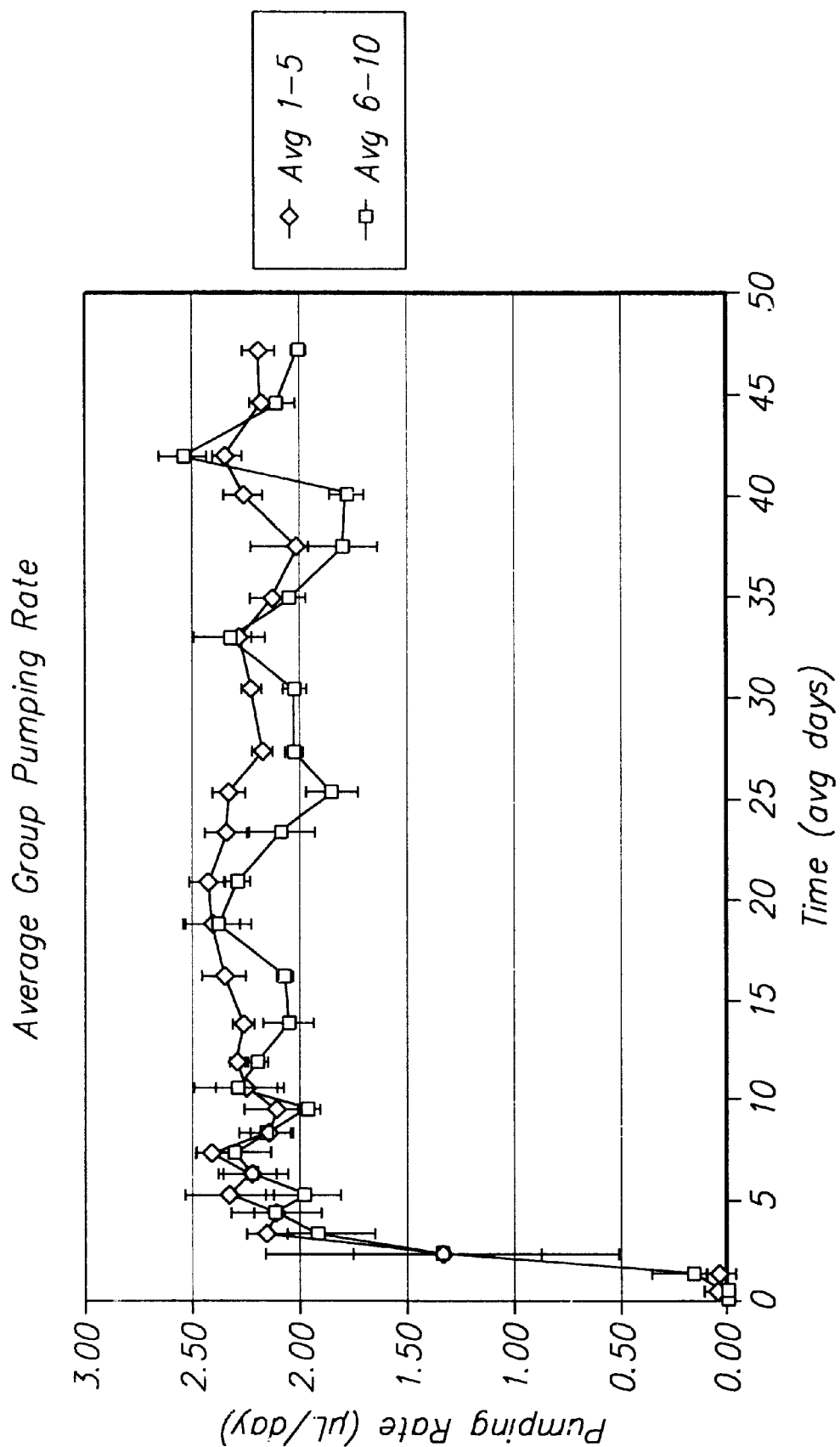
FIG. 8 is a graph showing the average pumping rates of the pumps of FIGS. 5 and 7.

The results for the 20 $\mu$g/hr system are provided in FIG. 5, with the cumulative release provided in FIG. 6. The results for the 5 $\mu$g/hr system are provided in FIG. 7. The average pumping rate for each group (the 20 $\mu$g/hr group of pumps and the 5 $\mu$g/hr group of pumps) is provided in FIG. 8. The results demonstrate that controlled, continuous, and precise low volume release of the potent opioid sufentanil is achieved with a DUROS™ osmotic implanted pump. In vitro release by the pump is correlated to in vivo release because the volume dispensed form the pump is a pure function of the pump and is independent of the environment surrounding the pump. Thus, these same pumps are expected to perform the same in vivo as in vitro.

What is claimed is:

1. A method of treating pain in a subject, the method comprising:
   completely implanting in a subject, at an implantation site, a controlled release drug delivery device comprising a pump and a formulation, the formulation comprising a drug selected from the group consisting of fentanyl and a fentanyl congener, wherein the formulation comprises an amount of the drug sufficient for treatment of pain in the subject for a period of at least about 3 days, and wherein the implantation site is selected from the group consisting of a subcutaneous site, a subdermal site, an intramuscular site, an intra-adipose tissue site, and an intra-lymphatic site; and
   parenterally delivering the formulation from the drug delivery device to the subject whereby the drug enters the systemic circulation and is thereby transported to a site of action, whereby the drug is present at the site of action in an amount sufficient to treat pain.

2. The method of claim 1, wherein the drug delivery device is implanted at a subcutaneous site.

3. The method of claim 1, wherein the formulation is delivered at a volume rate of from about 0.01 microliters per day to about 2 milliliters per day.

4. The method of claim 1, wherein the drug in the formulation is delivered at a rate of from about 0.01 micrograms per hour to 200 micrograms per hour.

5. The method of claim 1, wherein said delivering of the formulation is substantially continuous.

6. The method of claim 1, wherein the drug delivery device is coupled to a proximal end of a catheter for delivery of the formulation to a delivery site at a distance from the implantation site.

7. The method of claim 1, wherein the pump is selected from the group consisting of an electromechanical pump, an electroosmotic pump, a hydrolytic pump, a piezoelectric pump, an elastomeric pump, a vapor pressure pump, and an electrolytic pump.

8. The method of claim 1, wherein said delivering is for a period of from about 4 weeks to 12 months.

9. The method of claim 1, wherein the formulation comprises an amount of the drug sufficient to provide for treatment of pain in the subject for a period of more than 30 days.

10. The method of claim 1, wherein the formulation comprises an amount of the drug sufficient to provide for treatment of pain in the subject for a period of more than 100 days.

11. The method of claim 1, wherein the formulation comprises sufentanil.

12. The method of claim 11, wherein sufentanil is delivered at a rate of from about 0.01 $\mu$g/hr to about 200 $\mu$g/hr.

13. A method of treating pain in a subject, the method comprising:
   completely implanting in a subject, at an implantation site, a controlled release drug delivery device comprising a pump and a formulation comprising sufentanil, wherein the formulation comprises an amount of sufentanil sufficient for treatment of pain in the subject for a period of at least about 3 days, and wherein the implantation site is selected from the group consisting of a subcutaneous site, a subdermal site, an intramuscular site, an intra-adipose tissue site, and an intra-lymphatic site; and
   parenterally delivering the formulation to the subject whereby sufentanil enters the systemic circulation and is thereby transported to a site of action, and whereby sufentanil is present at the site of action in an amount sufficient to treat pain.

14. The method of claim 13, wherein the formulation comprises an amount of sufentanil sufficient for treatment of pain in the subject for a period of more than 20 days.

15. A method of treating pain in a subject suffering from pain, the method comprising:
   administering parenterally to the subject, from a completely implanted drug delivery device comprising a pump, a formulation comprising a drug selected from the group consisting of fentanyl and a fentanyl congener, wherein the device is implanted at an implantation site selected from the group consisting of a subcutaneous site, a subdermal site, an intramuscular site, all intra-adipose tissue site, and an intra-lymphatic site, said administering being at a volume rate of less than about 2 ml/day, wherein the drug enters the systemic circulation and is thereby transported to a site of action, and wherein said administering is for a period of at least about 3 days, and whereby the drug is present at the site of action in an amount sufficient to treat pain in the subject.

16. The method of claim 15, wherein the formulation comprises a drug present in a concentration of from about 1 mg/ml to about 450 mg/ml.

17. The method of claim 15, wherein the pump is selected from the group consisting of an electromechanical pump, an electroosmotic pump, a hydrolytic pump, a piezoelectric pump, an elastomeric pump, a vapor pressure pump, and an electrolytic pump.

18. The method of claim 15, wherein systemic delivery is substantially continuous.

19. The method of claim 15, wherein said administering is for a period of from about 4 weeks to 12 months.

20. The method of claim 15, wherein the formulation comprises sufentanil.

21. The method of claim 20, wherein sufentanil is delivered at a rate of from about 0.01 µg/hr to about 200 µg/hr.

22. The method of claim 20, wherein the formulation comprises an amount of sufentanil sufficient for treatment of pain in the subject for a period of more than 7 days.

23. The method of claim 20, wherein the formulation comprises an amount of sufentanil sufficient for treatment of pain in the subject for a period of more than 20 days.

24. A device for the treatment of pain, comprising:
a controlled drug delivery device adapted for complete implantation at an implantation site in a subject, the device comprising a pump and a formulation comprising a drug selected from the group consisting of fentanyl and a fentanyl congener, wherein the implantation site is selected from the group consisting of a subcutaneous site, a subdermal site, an intramuscular site, an intra-adipose tissue site, and an intra-lymphatic site, and wherein the formulation comprises an amount of the drug sufficient for treatment of pain in the subject for a period of at least about 3 days;
wherein the implantable device is adapted for parenteral delivery of the formulation to the subject for transport of the drug by the systemic circulation to a site of action in the subject, whereby the drug is present at the site of action in an amount effective for treatment of pain.

25. The device of claim 21, wherein the formulation comprises an amount of the drug sufficient for treatment of pain in the subject for a period of at least about 3 days to about 10 days.

26. The device of claim 24, wherein the formulation comprises an amount of the drug sufficient for treatment of pain in the subject for a period of at least about 4 weeks.

27. The device of claim 25, wherein the formulation comprises an amount of drug sufficient for treatment of pain in the subject for a period of at least about 100 days.

28. The device of claim 24, wherein the device delivers the formulation at a rate of from about 0.01 micrograms of the drug per hour to 200 micrograms of the drug per hour.

29. The device of claim 24, wherein the formulation comprises sufentanil.

30. The device of claim 24, wherein the device is adapted for delivery of the formulation at a volume rate of from about 0.01 microliters per day to 2 milliliters per day.

31. The device of claim 24, wherein the formulation comprises an amount of the drug sufficient for treatment of pain in the subject for a period of more than 7 days.

32. The device of claim 24, wherein the formulation comprises an amount of the drug sufficient for treatment of pain in the subject for a period of more than 20 days.

33. The device of claim 24, wherein the formulation comprises an amount of the drug sufficient for treatment of pain in the subject for a period of more than 30 days.

34. A method for treating pain in a subject, the method comprising:
implanting in a subject a controlled release drug delivery device, wherein said drug delivery device comprises a pump operatively connected to a housing, wherein said housing defines a reservoir and said reservoir contains a formulation, wherein said formulation comprises a drug selected from the group consisting of fentanyl and a fentanyl congener, and wherein said implanting is at a implantation site selected from the group consisting of a subcutaneous site, a subdermal site, an intramuscular site, an intra-adipose tissue site, and an intra-lymphatic site; and
delivering parenterally and systemically from said drug delivery device said formulation in an amount sufficient to treat pain in said subject for a period of at least about 3 days, and wherein said drug delivery device is completely implanted in said subject.

35. The method of claim 34, wherein the pump selected from the group consisting of: an electromechanical pump, and electroosmotic pump, an effervescent pump, a hydraulic pump, a piezoelectric pump, an elastomeric pump, a vapor pressure pump, and an electrolytic pump.

36. The method of claim 34 where said drug delivery device is implanted at a subcutaneous site.

37. The method of claim 34 wherein said formulation is delivered at a volume rate from about 0.01 microliters per day to about 2 milliliters per day.

38. The method of claim 34 wherein said delivering of said formulation is substantially continuous.

39. The method of claim 34 wherein said drug delivery device is coupled to a proximal end of a catheter for delivery of said formulation to a distal end of said catheter at location set apart from said drug delivery device.

40. The method of claim 34 wherein the drug is delivered at a rate from about 0.01 micrograms per hour to about 200 micrograms per hour.

41. The method of claim 13, wherein the drug delivery device is implanted at a subcutaneous site.

42. The method of claim 13, wherein the formulation is delivered at a volume rate of from about 0.01 microliters per day to about 2 milliliters per day.

43. The method of claim 13, wherein said delivering of the formulation is substantially continuous.

44. The method of claim 13, wherein said delivering is for a period of from about 4 weeks to 12 months.

45. The method of claim 13, wherein the drug delivery device comprises an amount of sufentanil sufficient to provide for treatment of pain in the subject for a period of more than 30 days.

46. The method of claim 13, wherein the drug delivery device comprises an amount of sufentanil sufficient to provide for treatment of pain in the subject for a period of more than 100 days.

47. The method of claim 1, wherein the pump comprises an osmotic pump.

48. The method of claim 15, wherein the pump comprises an osmotic pump.

49. The device of claim 24, wherein the pump is an osmotic pump.

50. The method of claim 1, wherein the drug is delivered at a rate of from about 3 micrograms per hour to 85 micrograms per hour.

51. The method of claim 1, wherein the drug is delivered at a rate of from about 5 micrograms per hour to 200 micrograms per hour.

52. The method of claim 13, wherein sufentanil is delivered at a rate of from about 3 micrograms per hour to 85 micrograms per hour.

53. The method of claim 13, wherein sufentanil is delivered at a rate of from about 5 micrograms per hour to 200 micrograms per hour.

54. The method of claim 15, wherein the drug is delivered at a rate of from about 3 micrograms per hour to 85 micrograms per hour.

55. The method of claim 15, wherein the drug is delivered at a rate of from about 5 micrograms per hour to 200 micrograms per hour.

56. The device of claim 25, wherein the device is adapted for delivery of drug at a rate of from about 3 micrograms per hour to 85 micrograms per hour.

57. The device of claim 24, wherein the device is adapted for delivery of drug at a rate of from about 5 micrograms per hour to 200 micrograms per hour.

58. The method of claim 34, wherein the drug is delivered at a rate of from about 3 micrograms per hour to 85 micrograms per hour.

59. The method of claim 34, wherein the drug is delivered at a rate of from about 5 micrograms per hour to 200 micrograms per hour.

60. The method of claim 13, wherein the drug delivery device comprises an amount of sufentanil sufficient for treatment of pain in the subject for a period of more than 30 days.

61. The method of claim 15, wherein the drug delivery device comprises an amount of drug sufficient for treatment of pain in the subject for a period of more than 30 days.

62. The device of claim 24, wherein the drug delivery device comprises an amount of drug sufficient for treatment of pain in the subject for a period of more than 30 days.

63. The method of claim 34, wherein the drug delivery device comprises an amount of drug sufficient for treatment of pain in the subject for a period of more than 30 days.

64. A device for the treatment of pain, comprising:

a controlled release drug delivery device adapted for complete implantation at an implantation site in a subject, the device comprising a pump and a formulation comprising sufentanil, wherein the formulation comprises an amount of sufentanil sufficient for treatment of pain in the subject for a period of at least about 3 days, and wherein the implantation site is selected from the group consisting of a subcutaneous site, a subdermal site, an intramuscular site, an intra-adipose tissue site, and an intra-lymphatic site; and wherein the drug delivery device is adapted for parenteral delivery of the formulation to the subject for transport of the drug by the systemic circulation to a site of action in the subject, whereby the drug is present at the site of action in an amount effective for treatment of pain.

65. The device of claim 64, wherein the drug delivery device comprises an amount of the drug sufficient for treatment of pain in the subject for a period of more than 30 days.

66. The device of claim 64, wherein the device is suitable for delivery of fentanyl or fentanyl congener at a volume rate of from about 0.01 microliters per day to 2 milliliters per day.

67. The device of claim 64, wherein the device is adapted for delivery of drug in the formulation at a rate of from about 3 micrograms per hour to 85 micrograms per hour.

68. The device of claim 64, wherein the device is adapted for delivery of drug in the formulation at a rate of from about 5 micrograms per hour to 200 micrograms per hour.

69. The device of claim 64, wherein the pump is an osmotic pump.

70. A device for treatment of pain, comprising:

a controlled release drug delivery device adapted for complete implantation at an implantation site in a subject, the device comprising a pump operably connected to housing, wherein said housing defines a reservoir and said reservoir comprises a formulation, wherein said formulation comprises a drug selected from the group consisting of fentanyl and a fentanyl congener, wherein the drug is in an amount sufficient for treatment of pain in the subject for a period of at least about 3 days, and wherein the implantation site is selected from the group consisting of a subcutaneous site, a subdermal site, an intramuscular site, an intra-adipose tissue site, and an intra-lymphatic site;

wherein the drug delivery device is adapted for parenteral delivery of the drug to the subject for transport of the drug by the systemic circulation to a site of action in the subject, whereby the drug is present at the site of action in an amount effective for treatment of pain.

71. The device of claim 70, wherein the drug delivery device comprises an amount of the drug sufficient for treatment of pain in the subject for a period of more than 30 days.

72. The device of claim 70, wherein the device is suitable for delivery of the drug at a volume rate of from about 0.01 microliters per day to 2 milliliters per day.

73. The device of claim 70, wherein the device is adapted for delivery of the drug in the formulation at a rate of from about 3 micrograms per hour to 85 micrograms per hour.

74. The device of claim 70, wherein the device is adapted for delivery of drug in the formulation at a rate of from about 5 micrograms per hour to 200 micrograms per hour.

75. The device of claim 70, wherein the pump is an osmotic pump.

76. The device of claim 70, wherein the drug is fentanyl.

77. The device of claim 70, wherein the drug is sufentanil.

78. The method of claim 1, wherein the drug is fentanyl.

79. The method of claim 15, wherein the drug is fentanyl.

80. The device of claim 24, wherein the drug is fentanyl.

81. The method of claim 34, wherein the drug is fentanyl.

82. The method of claim 1, wherein the formulation is delivered at a volume rate of less than 100 $\mu$l per day.

83. The method of claim 13, wherein the formulation is delivered at a volume rate of less than 100 $\mu$l per day.

84. The method of claim 15, wherein the formulation is delivered at a volume rate of less than 100 $\mu$l per day.

85. The device of claim 24, wherein the device is adapted for delivery of the formulation at a volume rate of less than 100 $\mu$l per day.

86. The method of claim 34, wherein the formulation is delivered at a volume rate of less than 100 $\mu$l per day.

87. The device of claim 64, wherein the device is adapted for delivery of the formulation at a volume rate of less than 100 $\mu$l per day.

88. The device of claim 70, wherein the device is adapted for delivery of the formulation at a volume rate of less than 100 $\mu$l per day.

* * * * *